(12) United States Patent
Kiyota et al.

(10) Patent No.: US 8,947,518 B2
(45) Date of Patent: Feb. 3, 2015

(54) CELL OBSERVING APPARATUS AND CELL INCUBATION METHOD

(75) Inventors: Yasujiro Kiyota, Tokyo (JP); Takayuki Uozumi, Machida (JP)

(73) Assignee: Nikon Corporation, Tokyo (JP)

( * ) Notice: Subject to any disclaimer, the term of this patent is extended or adjusted under 35 U.S.C. 154(b) by 23 days.

(21) Appl. No.: 13/552,839

(22) Filed: Jul. 19, 2012

(65) Prior Publication Data

US 2013/0027539 A1 Jan. 31, 2013

Related U.S. Application Data

(63) Continuation of application No. PCT/JP2011/000287, filed on Jan. 20, 2011.

(30) Foreign Application Priority Data

Jan. 20, 2010 (JP) ................................ 2010-010333

(51) Int. Cl.
*H04N 9/47* (2006.01)
*H04N 7/18* (2006.01)
*C12M 1/34* (2006.01)
(Continued)

(52) U.S. Cl.
CPC ........... *C12M 41/36* (2013.01); *G02B 21/0088* (2013.01); *G02B 21/32* (2013.01); *G02B 21/36* (2013.01)
USPC .......................................................... 348/79

(58) Field of Classification Search
CPC ....... G02B 21/365; G02B 21/367; H04N 7/18
USPC .......................................................... 348/79
See application file for complete search history.

(56) References Cited

U.S. PATENT DOCUMENTS

| 2011/0019923 A1* | 1/2011 | Mimura et al. ............... 382/203 |
| 2011/0091964 A1* | 4/2011 | Tateyama ................... 435/287.1 |
| 2011/0091965 A1 | 4/2011 | Tateyama |

FOREIGN PATENT DOCUMENTS

| JP | 2003-030638 | 1/2003 |
| JP | 2004-265237 | 9/2004 |

(Continued)

OTHER PUBLICATIONS

International Search Report of Corresponding PCT Application PCT/JP2011/00287 mailed Apr. 12, 2011.

(Continued)

*Primary Examiner* — Chikaodili E Anyikire
(74) *Attorney, Agent, or Firm* — Staas & Halsey LLP

(57) ABSTRACT

User's time and labor required for performing manipulations with respect to cells which exist in an incubation container, are reduced. To achieve the above, a cell observing apparatus includes an observation stage supporting an incubation container that houses cells, a micro imaging optical system forming, on an imaging device for micro imaging, an image of the cell in the incubation container disposed at an observing position of the observation stage, a macro imaging optical system forming, on an imaging device for macro imaging, an image of an area wider than that captured by the micro imaging optical system in the incubation container, and a controlling unit controlling an operation of a manipulation needle that manipulates the cells in the incubation container, in which the micro imaging optical system is disposed on a side facing the macro imaging optical system with the observation stage being located therebetween.

21 Claims, 13 Drawing Sheets

(51) Int. Cl.
*G02B 21/00* (2006.01)
*G02B 21/32* (2006.01)
*G02B 21/36* (2006.01)

(56) References Cited

FOREIGN PATENT DOCUMENTS

| | | |
|---|---|---|
| JP | 2005-287461 | 10/2005 |
| JP | 2008-139795 | 6/2008 |
| JP | 2009-78345 | 4/2009 |
| JP | 2009-198709 | 9/2009 |
| JP | 2009-229275 | 10/2009 |
| JP | 2010-4804 | 1/2010 |
| JP | 2010-4805 | 1/2010 |
| WO | 2009/119329 A1 | 10/2009 |

OTHER PUBLICATIONS

Japanese Office Action mailed Feb. 5, 2013 for corresponding Japanese Application No. 2011-550859.

International Preliminary Report on Patentability mailed Aug. 2, 2012 in corresponding International Patent Application No. PCT/JP2011/000287.

Written Opinion of the International Searching Authority issued Apr. 12, 2011 (English Translation mailed Aug. 16, 2012) in corresponding International Patent Application No. PCT/JP2011/000287.

"Generation of Human Induced Pluripotent Stem Cells", Center of iPS Cell Research and Application, Institute for Integrated Cell-Material Sciences, Kyoto University, Mar. 5, 2009, pp. 1-35.

International Search Report mailed Apr. 12, 2011 in corresponding PCT Application No. PCT/JP2011/000287.

Chinese Office Action issued Sep. 25, 2014 in corresponding Chinese Patent Application No. 201180006626.8.

Huixiang Wang et al. "Design of Micro-manipulation Instrument for Bio-microdissection", Habrbin Institute of Technology, Robotic Institute, Heilongjiang, Harbin, 150001, vol. 14 No. 3, Jun. 2006, pp. 416-421.

Ruiyun Peng et al., "Experimental cytology", Military Medical Science Press, $1^{st}$ edition (2008), Mar. 2008, pp. 13-14.

* cited by examiner

CELL OBSERVING APPARATUS AND CELL INCUBATION METHOD

CROSS REFERENCE TO RELATED APPLICATIONS

This application is a continuation application of international Application No. PCT/JP2011/000287, filed on Jan. 20, 2011, designating the U.S., in which the International Application claims a priority date of Jan. 20, 2010, based on prior filed Japanese Patent Application No. 2010-010333, the entire contents of which are incorporated herein by reference.

BACKGROUND

1. Field

The present application relates to a cell observing apparatus and a cell incubation method.

2. Description of the Related Art

A process of generating induced pluripotent stem cells (iPS cells) is disclosed in, for example, Non-Patent Document 1 (Center for iPS Cell Research and Application, Institute for Integrated Cell-Material Sciences, "Generation of Human induced Pluripotent Stem Cells", Kyoto University, Mar. 5, 2009).

In the process in Non-Patent Document 1, a feeder cell layer is first formed on a bottom surface of an incubation container that accommodates culture fluid, human adult skin cells (fibroblasts) are seeded on the layer, and then four genes called as Yamanaka factors are introduced into those cells (retroviral vectors for introducing the four genes are added). Thereafter, when the incubation is continued while changing the culture fluid, a cell colony in which the four genes are introduced and nothing else happens (Non-iPS cell colony) and a cell colony in which after the four genes are introduced, a differentiation potency is exhibited (iPS cell colony) appear, on the feeder cell, so that by picking up only the latter among the above using a syringe, the generation of iPS cell line is realized.

In this process, the picking of cell colony is manually performed by a skilled researcher while looking through an eyepiece lens of a microscope. At that time, the researcher sets an observation magnification of the microscope to a low-power side to observe a relatively wide range of the incubation container, and searches for the iPS cell colony. Subsequently, a stage is moved to dispose the cell colony in a vicinity of an optical axis of an objective lens, the observation magnification of the microscope is then set to a high-power side, and after the cell colony is confirmed as the iPS cell colony, the observation magnification of the microscope is returned to the low-power side, and a tip of the syringe is inserted into a dish to perform a picking of the cell colony.

However, when the cell colony was the Non-iPS cell colony, there was a need to reset the observation magnification of the microscope to the low-power side, to again search for a cell colony which seems like the iPS cell colony.

SUMMARY

The present invention has been made to solve the problems of the related art described above. A proposition of the present invention is to provide a cell observing apparatus and a cell incubation method effective for saving user's time and labor required for performing manipulations (injection, patch clamp, picking and so on) with respect to cells which exist in an incubation container.

A cell observing apparatus includes an observation stage supporting an incubation container that houses cells, a micro imaging optical system forming, on an imaging device for micro imaging, an image of the cell in the incubation container disposed at an observing position of the observation stage, a macro imaging optical system forming, on an imaging device for macro imaging, an image of an area wider than that captured by the micro imaging optical system in the incubation container, and a controlling unit controlling an operation of a manipulation needle that manipulates the cells in the incubation container, in which the micro imaging optical system is disposed on a side facing the macro imaging optical system with the observation stage being located therebetween.

Note that it is also possible that the controlling unit moves the manipulation needle to a position at which a picking of the cell in the incubation container can be performed based on a wide image obtained by the imaging device for macro imaging and a partial image obtained by the imaging device for micro imaging.

Further, it is also possible that the controlling unit decides a focused cell being a cell to be focused among the cells in the incubation container based on an image analysis of a wide image obtained by the imaging device for macro imaging, calculates position coordinates of the focused cell, and then controls the manipulation needle based on the wide image obtained by the imaging device for macro imaging and a partial image obtained by the imaging device for micro imaging.

Further, it is also possible that the controlling unit moves the manipulation needle to the position coordinates of the cell being a manipulation target based on the wide image obtained by the imaging device for macro imaging and makes the manipulation needle to be positioned at the position coordinates of the cell based on the partial image obtained by the imaging device for micro imaging when controlling the manipulation needle.

Further, it is also possible that the micro imaging optical system and the macro imaging optical system are configured coaxially.

Further, it is also possible that the micro imaging optical system is disposed on a side of a bottom portion of the incubation container.

Further, it is also possible that the controlling unit controls the manipulation needle to perform a picking of a target cell from the incubation container based on the partial image obtained by the imaging device for micro imaging, and seeds the target cell obtained through the picking in another incubation container.

Further, a cell incubation method is a cell incubation method of incubating cells using the cell observing apparatus, increasing a number of the target cell by repeatedly conducting, a step seeding the target cell obtained through the picking in the other incubation container, and then transferring the other incubation container to an incubator, and a step incubating the seeded target cell for a certain period of time in the incubator, and then returning the other incubation container to the cell observing apparatus.

Note that the target cell may also be an iPS cell.

Further, a cell observing apparatus includes an observation stage supporting an incubation container that houses cells, a micro imaging optical system forming, on an imaging device for micro imaging, an image of the cell in the incubation container disposed at an observing position of the observation stage, a macro imaging optical system forming, on an imaging device for macro imaging, an image of an area wider than that captured by the micro imaging optical system in the incubation container, and a controlling unit controlling an operation of a manipulation needle that manipulates the cells in the incubation container, in which the controlling unit realizes both of an obtainment of a wide image by the imaging device for macro imaging and an obtainment of a partial image by the imaging device for micro imaging at a same time when controlling the manipulation needle.

Note that it is also possible that there is further provided an oblique illuminating optical system illuminating the incubation container on the observation stage with an illumination luminous flux which is not parallel to optical axes of the macro imaging optical system and the micro imaging optical system.

Further, it is also possible that the controlling unit displays, in real time, both of a wide dark-field image obtained by the imaging device for macro imaging during a period of time in which the oblique illuminating optical system is turned on, and a partial dark-field image obtained by the imaging device for micro imaging during the period of time.

Further, it is also possible that the cell observing apparatus further includes an excitation light illuminating optical system irradiating excitation light to the cells in the incubation container, and a storing unit obtaining, through the imaging device for micro imaging, partial fluorescence images from respective parts of the incubation container to which the excitation light is irradiated, and previously storing histories of the respective parts, in which the controlling unit reads the history of the part, in the incubation container, positioned on the optical axis of the micro imaging optical system, from the storing unit, and displays the history together with the partial dark-field image which is being displayed in real time.

Further, it is also possible that the controlling unit displays the history as a movie image.

Further, it is also possible that the controlling unit reads latest partial fluorescence images of the respective parts of the incubation container from the storing unit, and superimpose displays a guiding image in which the partial fluorescence images are connected, on the wide dark-field image which is being displayed in real time.

Further, it is also possible that the controlling unit automatically adjusts the observation stage to make a manipulation target candidate position on the optical axis of the micro imaging optical system when the manipulation target candidate in the incubation container is designated on the guiding image.

Further, it is also possible that, when a manipulation target candidate in the incubation container is designated on the guiding image and a completion notification of manipulation with respect to the manipulation target candidate is input, the controlling unit highlights the manipulation target candidate on the guiding image.

Further, it is also possible that the controlling unit simultaneously displays the wide image obtained by the imaging device for macro imaging, the partial image obtained by the imaging device for micro imaging, and the movie image.

Further, it is also possible that, when an arbitrary cell is designated from the wide image, the controlling unit displays the movie image of the designated cell.

A cell incubation method of incubating cells, increasing a number of good cell by repeatedly conducting a micro imaging step performing a micro observation of the cell which is being incubated in an incubation container, to obtain a partial image, a macro imaging step performing a macro observation of an area wider than that in the micro imaging step in the incubation container, to obtain a wide image, a judging step judging a state of the cell based on the partial image, a picking step controlling, based on the wide image and the partial image, a manipulation needle to perform a picking of the good cell whose state is judged as good, from the incubation container, a step seeding the good cell picked up by the manipulation needle, in another incubation container, and then transferring the other incubation container to an incubator, and an incubating step incubating the seeded good cell in the incubator for a certain period of time.

Note that it is also possible that in the picking step, an XY coordinate position of the manipulation needle is made to coincide with an XY coordinate position of the cell based on the wide image obtained in the macro imaging step, the manipulation needle is driven toward an XYZ coordinate position of the cell based on the partial image obtained in the micro imaging step, and the cell is picked up by the manipulation needle.

Further, the cell may also be an iPS cell.

DETAILED DESCRIPTION OF THE EMBODIMENTS

First Embodiment

Hereinafter, embodiments of a cell observing system will be described as embodiments of the present invention.

Figure 1:
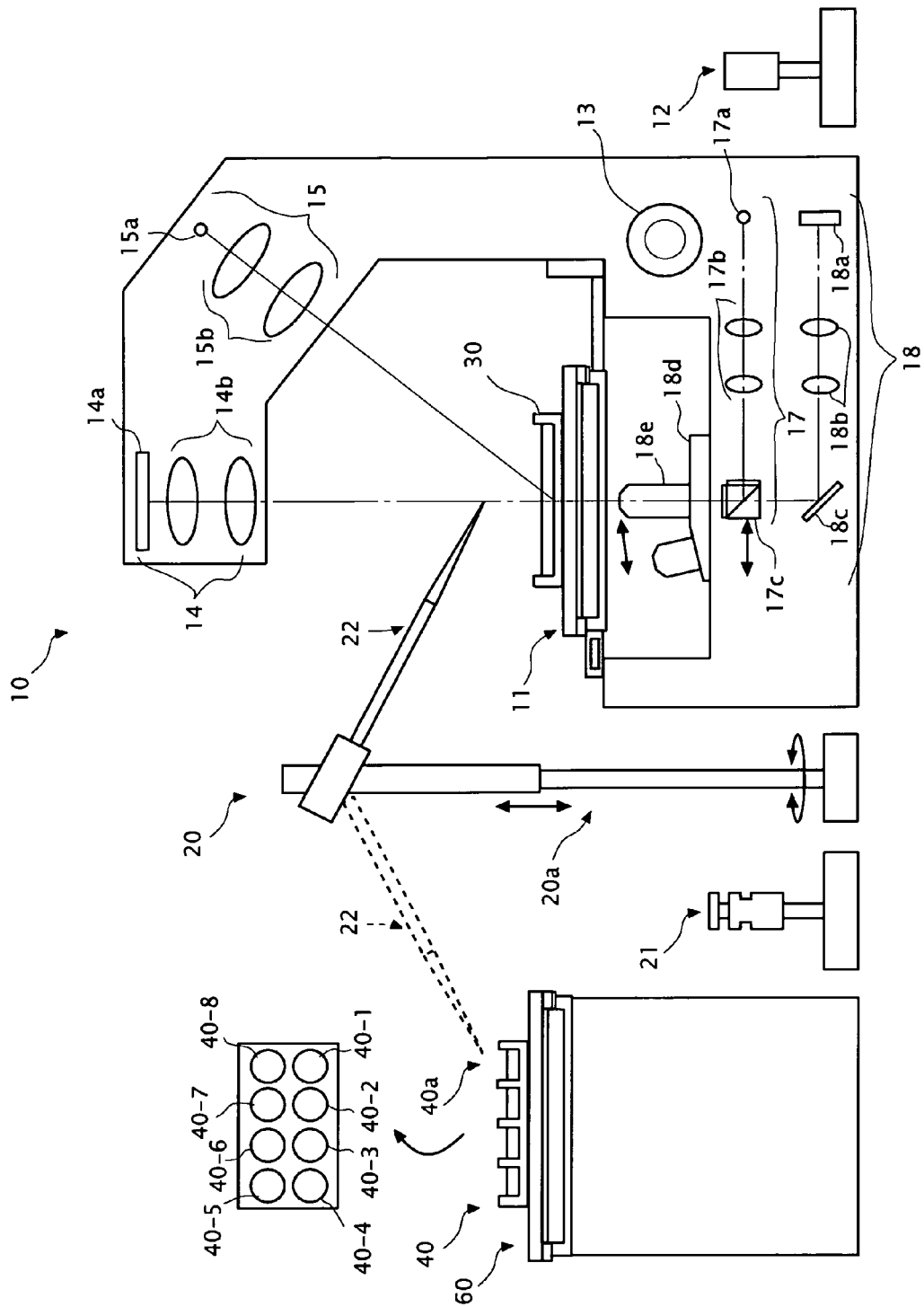
FIG. 1 is a diagram explaining a configuration of a mechanical part of the present system.

FIG. 1 is a diagram explaining a configuration of a mechanical part of the present system. As illustrated in FIG. 1, in the present system, there are provided an inverted microscope 10 for observing cells in an incubation container 30, a manipulator 20 for manipulating the cells in the incubation container 30, an electrically-operated reserve stage 60 that supports a reserve container 40, a manipulator controller 21 for driving the manipulator 20, and a stage controller 12 for driving an observation stage 11 of the inverted microscope 10. Note that the present system also includes a not-illustrated computer (explanation of the computer will be made later).

In the inverted microscope 10, there are provided the transmission-type and electrically-operated observation stage 11 that supports the incubation container 30, a macro imaging optical system (stereomicroscope) 14 that obtains an entire image of the incubation container 30 from above and front of the incubation container 30, a micro imaging optical system (magnifying microscope) 18 that obtains a magnified image of a part of the incubation container 30 from below and front of the incubation container 30, an oblique illuminating optical system 15 that illuminates the entire incubation container 30 from a diagonally upward direction of the incubation container 30, a fluorescence epi-illumination optical system 17 that irradiates excitation light to a part of the incubation container 30 from below and front of the incubation container 30 through an objective lens 18e of the micro imaging optical system 18, and a focus knob 13 with which a user manually performs focusing of the objective lens 18e with respect to the incubation container 30.

The incubation container 30 is, for example, a dish with a diameter of 100 mm. On a bottom surface of the incubation container 30, a feeder cell layer is formed, and an upper part of the feeder cell layer is filled with culture fluid. Further, on the feeder cell layer, human adult skin cells (fibroblasts) are previously seeded, and to those cells, retroviral vectors for introducing four genes called as Yamanaka factors are added. Note that in these cells, a fluorescence gene that generates fluorescence of specific color (green color in this case) only when a differentiation potency is exhibited after the introduction of four genes, is previously introduced.

In this incubation container 30, a cell adhered to a surface of the feeder cell layer is proliferated to form a cell colony. In order to observe the cell colony, in the aforementioned focusing, a focal plane of the objective lens 18e of the micro imaging optical system 18 is positioned in the vicinity of the bottom surface of the incubation container 30 (in the vicinity of the feeder cell layer).

The observation stage 11 fixes and holds the incubation container 30 with a holder suitable for a shape of the incubation container 30. Accordingly, even if the incubation container 30 is temporarily removed from the observation stage 11 for the purpose of the change of the culture fluid or the like, a posture and a disposed position of the incubation container 30 with respect to the observation stage 11 are reproduced. Further, the observation stage 11 is connected to the stage controller 12, and when a user operates the stage controller 12, the observation stage 11 makes, in accordance with the operation contents, the incubation container 30 move in directions (XY directions) along a mounting table of the observation stage 11.

Figure 2:
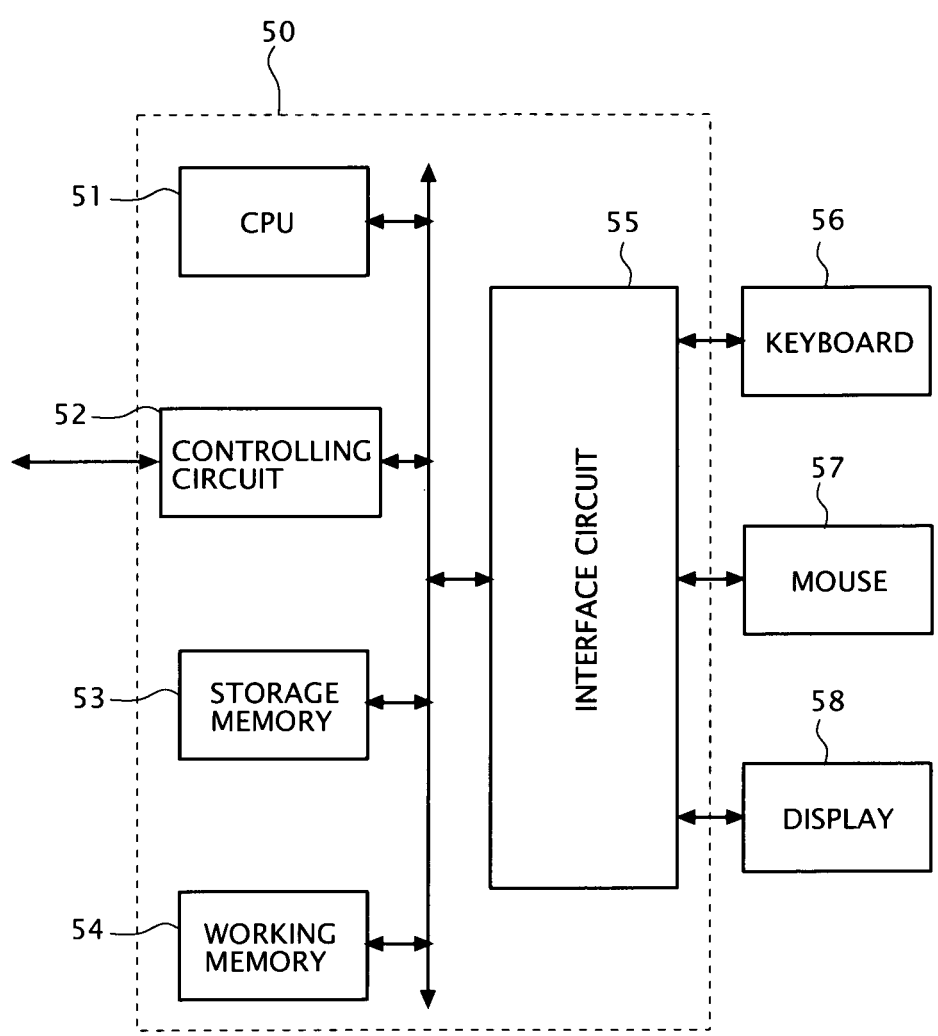
FIG. 2 is a diagram explaining a computer of the present system.

Note that although the observation stage 11 and the stage controller 12 may also be directly connected, here, for convenience of explanation, it is assumed that they are indirectly connected via a controlling circuit of the computer (FIG. 2).

The micro imaging optical system 18 includes an electrically-operated revolver 18d that holds a plurality of objective lenses, a light deflecting mirror 18c, an imaging optical system 18b, and an imaging device 18a, and obtains a magnified image (an image magnified 10 times, for example) of an area (partial area), in the incubation container 30, captured by a field of view of the objective lens 18e. Note that an optical axis of the objective lens 18e of the micro imaging optical system 18 is vertical to a reference plane of the observation stage 11.

The revolver 18d holds the plurality of objective lenses with different magnifications, and switches the objective lens 18e of the micro imaging optical system 18 to another objective lens. Accordingly, an observation magnification of the micro imaging optical system 18 is switched between 10-power and 4-power, for example.

The macro imaging optical system 14 includes imaging lenses 14b and an imaging device 14a, and obtains a reduced image (an image reduced to half, for example) of the entire incubation container 30. With the imaging lenses 14b, the vicinity of the incubation container 30 and an imaging area of the imaging device 14a are coupled in a conjugate relation, and even if the focusing is not performed, it is possible to form the entire image of the incubation container 30 on the imaging area with a sufficient contrast. Note that an optical axis of the imaging lenses 14b coincides with the optical axis of the objective lens 18e of the micro imaging optical system 18.

The oblique illuminating optical system 15 includes a light source for oblique illumination 15a formed of a white light source or the like, and illuminating lenses 15b, and illuminates the entire incubation container 30 from a diagonal direction with a substantially uniform illuminance. Note that an optical axis of the illuminating lenses 15b intersects the optical axis of the macro imaging optical system 14 in the vicinity of the mounting table of the observation stage 11.

It is set that, out of the light emitted from the light source for oblique illumination 15a and passing through the illuminating lenses 15b, scattered light generated at the incubation container 30 is incident on the macro imaging optical system 14 and the objective lens 18e of the micro imaging optical system 18, but, non-scattered light (direct light) generated at the incubation container 30 is not incident on the macro imaging optical system 14 and the objective lens 18e of the micro imaging optical system 18 almost at all.

Accordingly, when the light source for oblique illumination 15a is turned on, the micro imaging optical system 18 can obtain a magnified dark-field image of the aforementioned partial area of the incubation container 30 (referred to as "micro dark-field image", hereinafter). Further, when the light source for oblique illumination 15a is turned on, the macro imaging optical system 14 can obtain a reduced dark-field image of the entire incubation container 30 (referred to as "macro dark-field image", hereinafter).

The fluorescence epi-illumination optical system 17 includes an excitation light source 17a, illuminating lenses 17b, and a fluorescence block 17c, and irradiates excitation light to the aforementioned partial area via the objective lens 18e of the micro imaging optical system 18. Note that an emission wavelength of the excitation light source 17a is set to a wavelength for exciting a fluorescent material exhibited in a cell, and a detection wavelength of the fluorescence block 17c is set to a wavelength same as a wavelength of fluorescence emitted by the fluorescent material (a wavelength of green color, in this case).

Accordingly, when the excitation light source 17a is turned on, the micro imaging optical system 18 can obtain a magnified fluorescence image of the aforementioned partial area of the incubation container 30 (referred to as "micro fluorescence image", hereinafter).

Note that the fluorescence block 17c of the fluorescence epi-illumination optical system 17 is configured to be capable of being inserted/removed into/from an optical path of the micro imaging optical system 18, and the insertion/removal is performed by a not-illustrated electrical mechanism. When the micro imaging optical system 18 obtains the micro dark-field image, the fluorescence block 17c is removed from the optical path, and when the micro imaging optical system 18 obtains the micro fluorescence image, the fluorescence block 17c is inserted into the optical path.

The manipulator 20 is, for example, a hydraulic manipulator, and a manipulation needle for manipulating cells in the incubation container 30, is attached thereto. Here, it is assumed that a syringe 22 is attached as the manipulation needle. Note that a tip portion of the syringe 22 can be changed with a new one, in accordance with need.

The manipulator 20 is provided on a base common to the inverted microscope 10, at a position separated from the inverted microscope 10, and supports a pump part of the syringe 22 with the tip of the syringe 22 directed diagonally downward. The manipulator 20 rotates the syringe 22 around a rotating shaft 20a parallel to the optical axis of the macro imaging optical system 14, or makes the syringe 22 shift in a direction along the rotating shaft 20a.

Further, the manipulator 20 can set a combination of a rotation position and a shift position of the syringe 22 to an observing mode (mode illustrated by a solid line in FIG. 1) which is previously determined according to need. Further, the manipulator 20 can set a combination of the rotation position and the shift position of the syringe 22 to a separating mode (mode illustrated by a dotted line in FIG. 1) which is previously determined according to need.

The observing mode illustrated by the solid line in FIG. 1 is a mode in which the tip of the syringe 22 is disposed on the optical axis of the macro imaging optical system 14, and the tip of the syringe 22 is positioned above the uppermost portion of the incubation container 30. When the syringe 22 is in this observing mode, even if the observation stage 11 is tentatively moved in the XY directions, there is no chance that the syringe 22 is brought into contact with the incubation container 30. Further, when the shift position of the syringe 22 is displaced downward from this observing mode, it is possible to make the tip of the syringe 22 dip in the culture fluid in the incubation container 30.

The separating mode illustrated by the dotted line in FIG. 1 is a mode in which the entire syringe 22 is completely separated from the inverted microscope 10. The aforementioned reserve stage 60 disposes, at a position below the tip of the syringe 22 in the separating mode (a reserve position indicated by a reference numeral 40a in FIG. 1), a reservoir of the reserve container 40.

Further, the manipulator 20 is connected to the manipulator controller 21, and when the user operates the manipulator controller 21, the manipulator 20 drives the syringe 22 in accordance with the contents of the operation.

Note that although the manipulator 20 and the manipulator controller 21 may also be directly connected, here, for convenience of explanation, it is assumed that they are indirectly connected via the controlling circuit of the computer (FIG. 2).

Further, although the pump part of the syringe 22 may also be directly manually operated by the user, here, for convenience of explanation, it is assumed that the pump part is electrically operated, and is driven by the manipulator 20. In this case, the user performs each of suction of fluid (here, the culture fluid including cells is called as "fluid") into the syringe 22, and ejection of the fluid from the syringe 22, through the operation of the manipulator controller 21.

The reserve stage 60 fixes and holds the reserve container 40 with the holder suitable for the shape of the reserve container 40. In the reserve container 40, a plurality of reservoirs 40-1 to 40-8 are formed by being arranged in an XY plane in a state of facing respective openings thereof upward.

Therefore, if the fluid is ejected from the syringe 22 when the syringe 22 is in the separating mode, the fluid can be reserved in the reservoir (available reservoir) disposed at the reserve position 40a. Further, when the reserve stage 60 moves the reserve container 40 in the XY directions, it is possible to switch the available reservoir among the reservoirs 40-1 to 40-8.

FIG. 2 is a diagram explaining the computer of the present system. As illustrated in FIG. 2, a computer 50 of the present system includes a controlling circuit 52, a CPU 51, a storage memory 53, a working memory 54, and an interface circuit 55.

Among the above, the controlling circuit 52 is connected to the observation stage 11, the revolver 18d, the imaging devices 14a and 18a, the fluorescence block 17c, the light source for oblique illumination 15a, the excitation light source 17a, the reserve stage 60, the stage controller 12, and the manipulator controller 21 illustrated in FIG. 1.

Further, in the computer 50, an operation program for the CPU 51 is previously installed. This operation program is stored in the storage memory 53, and is read on the working memory 54 according to need, to be executed by the CPU 51.

Further, to the computer 50, input/output devices such as a keyboard 56, a mouse 57, and a display 58 are connected via the interface circuit 55. The user can input various instructions into the CPU 51 of the computer 50 via the keyboard 56 or the mouse 57. Note that the transmission/reception of information between the computer 50 and the user is set to be conducted through a well-known GUI utilizing the keyboard 56, the mouse 57, and the display 58.

The information which is input into the computer 50 by the user includes an observing schedule of the incubation container 30, a start instruction of observation, a start instruction of picking assistance, and the like.

The observing schedule indicates an observation frequency with respect to the incubation container 30, and is set as "every 24 hours" or the like, for example. This observing schedule is stored in the storage memory 53.

The start instruction of observation is an instruction which is input when a preparation of the incubation container 30 is completed and the incubation is started, and is an instruction for making the CPU 51 execute observation processing (which will be described later).

The start instruction of picking assistance is an instruction which is input when a picking of necessary cell (iPS cell colony, in this case) is performed after the incubation is conducted over a sufficient period of time, and is an instruction for making the CPU 51 execute picking assistance processing (which will be described later).

Figure 3:
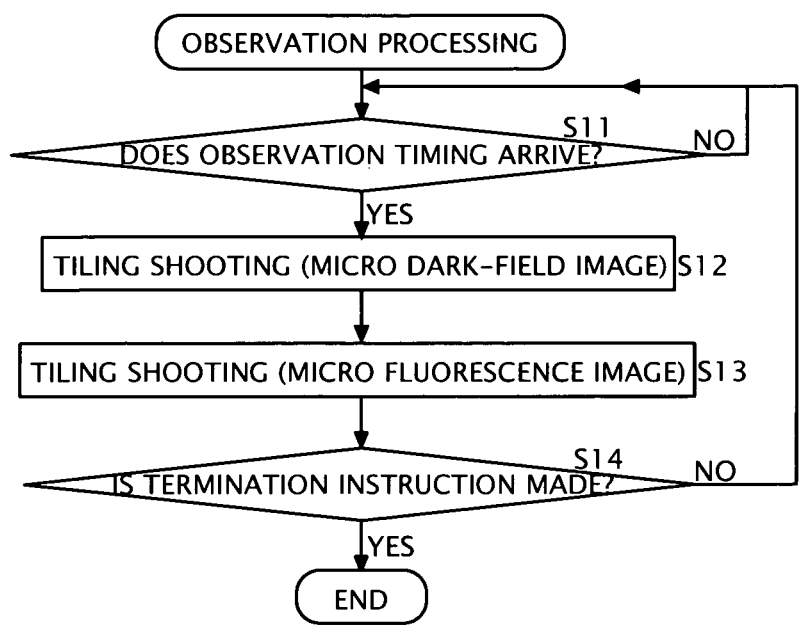
FIG. 3 is a flow chart of observation processing performed by a CPU 51.

FIG. 3 is a flow chart of the observation processing performed by the CPU 51. Hereinafter, respective steps in FIG. 3 will be described in order. Note that it is set that, when executing the observation processing, the tip of the syringe 22 is removed from the syringe 22.

Step S11: The CPU 51 reads the observing schedule stored in the storage memory 53, and compares the observing schedule with current time and date, to thereby judge whether an observation timing arrives or not. When the observation timing arrives, the process proceeds to step S12, and when the observation timing does not arrive, the CPU 51 stands by.

Step S12: The CPU 51 instructs the controlling circuit 52 to perform tiling shooting with oblique illumination. The controlling circuit 52 drives the fluorescence block 17c according to need to remove the fluorescence block 17c from the optical path of the micro imaging optical system 18, and drives the revolver 18d according to need to insert the objective lens for 10-power observation into the optical path of the micro imaging optical system 18. Under this state, by turning on the light source for oblique illumination 15a, and repeatedly driving the imaging device 18a while step-moving the observation stage 11 in the XY directions, the controlling circuit 52 obtains a plurality of micro dark-field images which individually covers respective partial areas of the incubation container 30, and turns off the light source for oblique illumination 15a.

The CPU 51 gives, to each of the plurality of micro dark-field images obtained by the controlling circuit 52, coordinate information on the incubation container of the corresponding partial area (container coordinate information), and then writes those micro dark-field images into the storage memory 53. Note that when performing the writing, the CPU 51 gives information of current time and date (observing time and date) to each of these micro dark-field images.

Step S13: The CPU 51 gives an instruction to the controlling circuit 52 to perform tiling shooting with the excitation light source. The controlling circuit 52 drives the fluorescence block 17c to insert the block into the optical path of the micro imaging optical system 18. Under this state, by turning on the excitation light source 17a, and repeatedly driving the imaging device 18a while moving the observation stage 11 in a movement pattern same as that of step S13, the controlling circuit 52 obtains a plurality of micro fluorescence images which individually covers respective partial areas of the incubation container 30, and turns off the excitation light source 17a.

The CPU 51 gives, to each of the plurality of micro fluorescence images obtained by the controlling circuit 52, coordinate information on the incubation container of the corresponding partial area (container coordinate information), and then writes those micro fluorescence images into the storage memory 53. Note that when performing the writing, the CPU 51 gives information of current time and date (observing time and date) to these micro fluorescence images. Note that in this case, it is assumed that a portion with high brightness in the micro fluorescence image is represented by a color same as the color corresponding to the detection wavelength of the fluorescence block 17c (green color, in this case).

Step S14: The CPU 51 judges whether or not a termination instruction is input by the user, in which when the instruction is not input, the process returns to step S11, and when the termination instruction is input, the flow is terminated.

Therefore, every time the observation timing arrives, the CPU 51 obtains the micro dark-field images and the micro fluorescence images regarding the respective partial areas of the incubation container 30, and writes the images into the storage memory 53. Accordingly, a history of the micro dark-field images and a history of the micro fluorescence images are gradually accumulated for each partial area of the incubation container 30.

Figure 4:
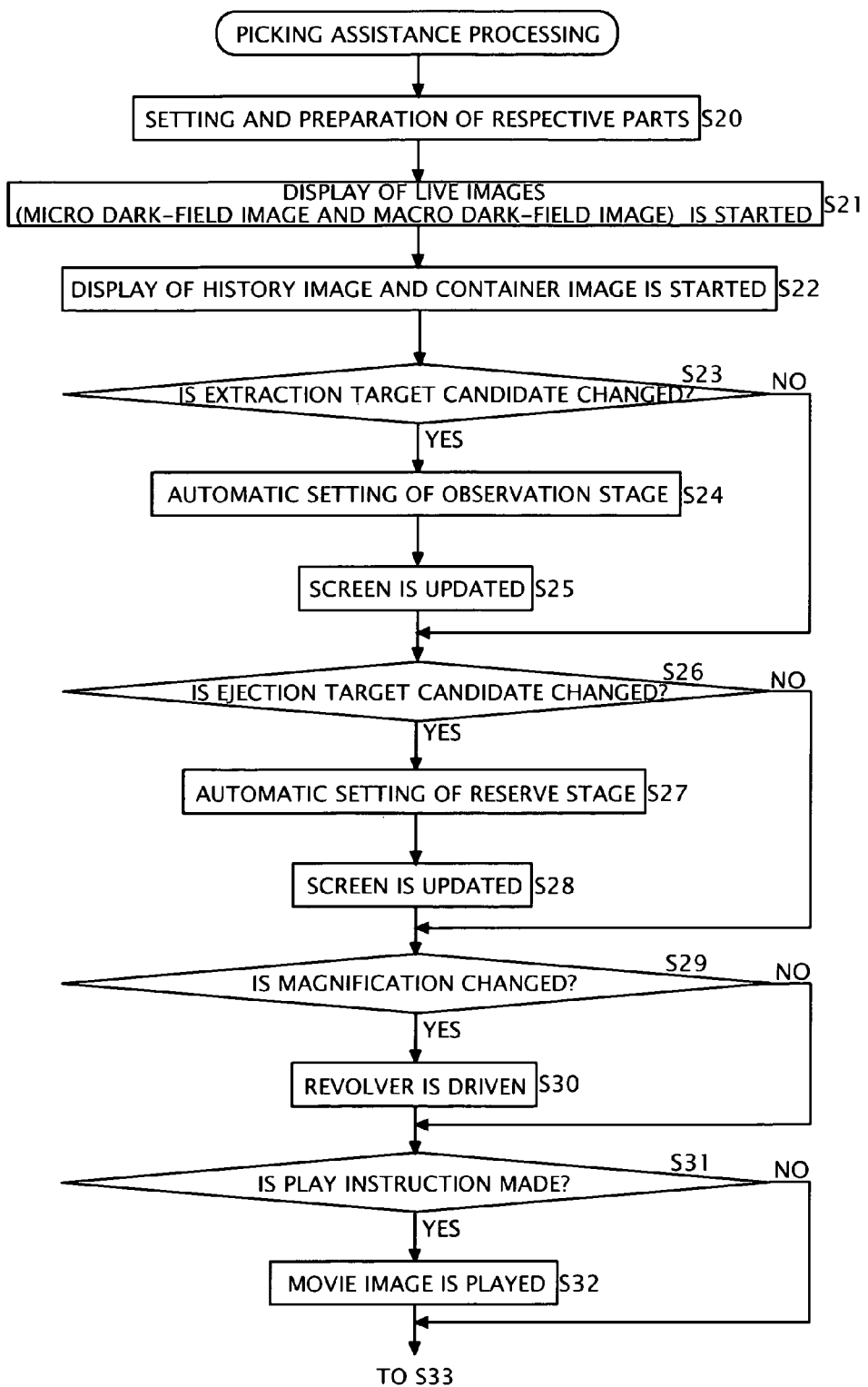
FIG. 4 is a flow chart (first half) of picking assistance processing performed by the CPU 51.
Figure 5:
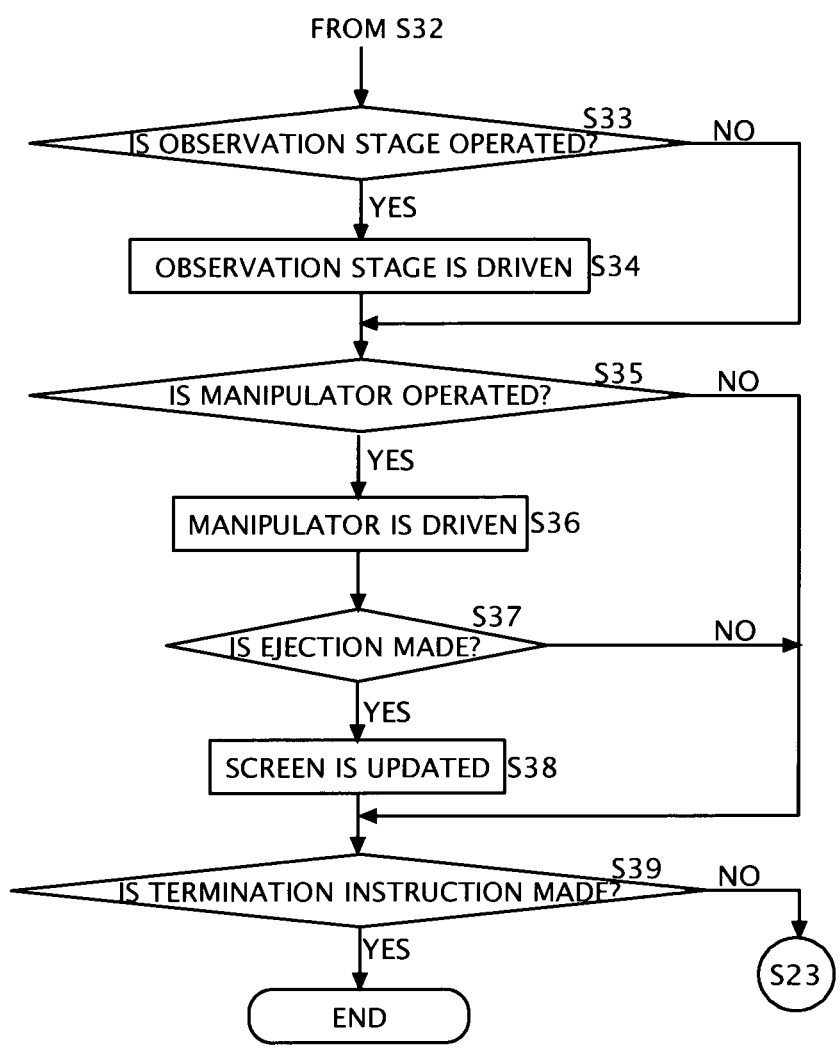
FIG. 5 is a flow chart (second half) of the picking assistance processing performed by the CPU 51.

FIG. 4 and FIG. 5 are flow charts of the picking assistance processing performed by the CPU 51. Hereinafter, respective steps in FIG. 4 and FIG. 5 will be described in order. Note that although the user performs attachment or change of the tip of the syringe 22 according to need, in the middle of the picking assistance processing, here, for simplification of explanation, it is assumed that the tip of the syringe 22 is attached when starting the picking assistance processing, and is then continuously used without change.

Step S20: The CPU 51 reads the images (the plurality of micro dark-field images and the plurality of micro fluorescence images) for each partial area stored in the storage memory 53, and based on those images, the CPU 51 creates a time lapse movie image for each partial area, and stores it in the storage memory 53. Note that the creation of time lapse movie image for each partial area is conducted in the following manner. Specifically, the CPU 51 synthesizes each of the two images covering the same partial area and having the same observing time and date, among the plurality of micro dark-field images and the plurality of micro fluorescence images, into one image, and connects a plurality of synthesized images obtained through such synthesis, in an order of the observing time and date. The time lapse movie image created as above corresponds to the time lapse movie image of the partial area.

Further, the CPU 51 gives an instruction to the controlling circuit 52 to set each part of the system to an initial state. The controlling circuit 52 drives the manipulator 20 according to need, to set the syringe 22 to be in the observing mode, and drives the observation stage 11 according to need, to dispose a center of the incubation container 30 on the optical axis of the macro imaging optical system 14 (=the optical axis of the objective lens 18e of the micro imaging optical system 18). Hereinafter, the optical axis is simply referred to as "optical axis".

Further, the controlling circuit 52 drives the fluorescence block 17c according to need to remove the fluorescence block 17c from the optical path of the micro imaging optical system 18, and drives the revolver 18d according to need to insert the objective lens for 10-power observation into the optical path of the micro imaging optical system 18.

Further, the controlling circuit 52 drives the reserve stage 60 according to need to set the available reservoir to a first reservoir (the reservoir 40-1).

Step S21: The CPU 51 gives an instruction to the controlling circuit 52 to start a display of live image.

The controlling circuit 52 turns on the light source for oblique illumination 15a, and starts continuous driving of both of the imaging device 18a of the micro imaging optical system 14 and the imaging device 14a of the macro imaging optical system 18. Accordingly, the micro dark-field images and the macro dark-field images start to be obtained continuously and in a parallel manner.

Figure 6:
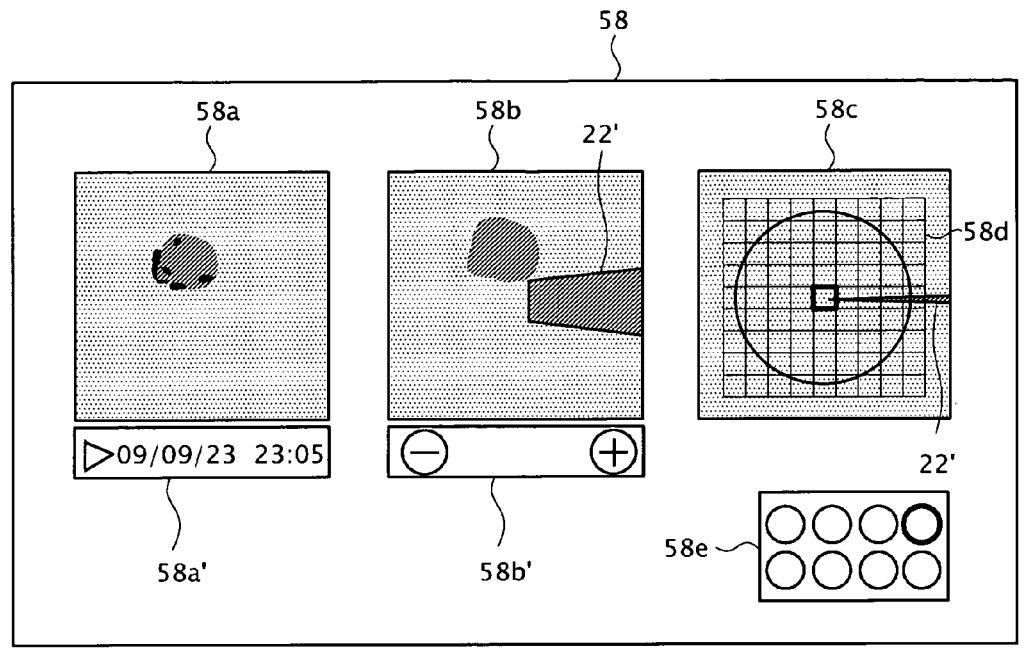
FIG. 6 is a diagram illustrating an initial display screen of a display 58.

The CPU 51 starts sequentially outputting the micro dark-field images sequentially obtained by the controlling circuit 52, on a predetermined area on the display 58 as indicated by a reference numeral 58b in FIG. 6, and it starts sequentially outputting the macro dark-field images sequentially obtained by the controlling circuit 52, on another predetermined area on the display 58 as indicated by a reference numeral 58c in FIG. 6.

Therefore, on the display 58, the live image 58b of the micro dark-field image (referred to as "micro live image 58b", hereinafter) and the live image 58c of the macro dark-field image (referred to as "macro live image 58c", hereinafter) start to be simultaneously displayed.

Further, the CPU 51 displays a magnification change button 58b', in the vicinity of the micro live image 58b on the display 58. The magnification change button 58b' is a button with which the user inputs an instruction of changing the observation magnification, into the computer 50.

Note that at this moment, the syringe 22 is set to be in the observing mode, so that a dark-field image 22' of the syringe 22 is also captured in the micro live image 58b and the macro live image 58c. If it is assumed that a center of the micro live image 58b corresponds to the optical axis, and a center of the macro live image 58c corresponds to the optical axis, a dark-field image of the tip of the syringe 22 is positioned at a center of each of the micro live image 58b and the macro live image 58c. When only the observation stage 11 is driven (when the manipulator 20 is not driven) under this state, a dark-field image of the incubation container 30 moves on the micro live image 58b and the macro live image 58c, and the dark-field image 22' of the syringe 22 does not move.

Step S22: The CPU 51 reads, out of the micro fluorescence images stored for each partial area in the storage memory 53, the micro fluorescence images with the latest observing time and date, performs size reduction processing on the micro fluorescence images, and arranges the processed images in an order of the container coordinates, to thereby create a tiling fluorescence image. This tiling fluorescence image is used as a guiding image.

The CPU 51 performs brightness reduction processing on this tiling fluorescence image, and superimpose displays the processed tiling fluorescence image on the macro live image 58*c* (a reference numeral 58*d* in FIG. 6). Note that when superimpose displaying, the CPU 51 adjusts a superimposing position of the tiling fluorescence image 58*d*, so that a center of the container in the tiling fluorescence image 58*d* coincides with a center of the container in the macro live image 58*c*.

Figure 7:
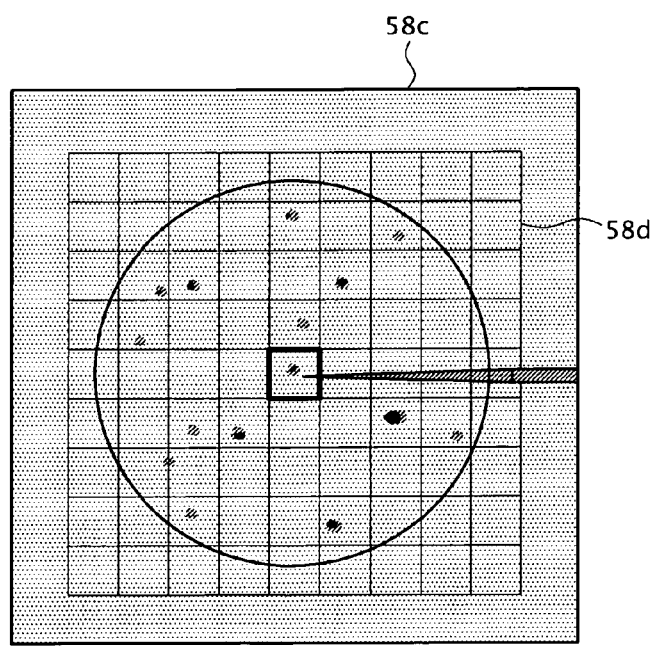
FIG. 7 is a diagram explaining a macro live image 58c and a tiling fluorescence image 58d.

Therefore, on the macro live image 58*c*, a current state (a texture, a size, and the like) of cell colonies dotted in the incubation container 30 and a recent degree of fluorescence of those cell colonies are simultaneously visualized, as illustrated in FIG. 7 in an enlarged manner. Note that in FIG. 7, an area, in the tiling fluorescence image 58*d*, which should be represented by green color (an area that exhibits fluorescence) is represented by filling the area (the same applies to the other respective drawings). The user can easily find out a cell colony which seems like an iPS cell colony, on such a macro live image 58*c*.

Further, the CPU 51 of the present step highlights a partial area disposed at a position of the optical axis, out of the plurality of micro fluorescence images (the plurality of partial areas) that form the tiling fluorescence image 58*d*, as an extraction target candidate of cell. Hereinafter, it is set that the highlighting of the partial area is performed by thickening a contour line of the partial area, as illustrated in FIG. 6 and FIG. 7.

Note that when the user selects a partial area which is not highlighted on the tiling fluorescence image 58*d*, it is possible to cancel the designation of the extraction target candidate at the present moment, and to designate the selected partial area as a new extraction target candidate.

Note that the designation of the partial area by the user is conducted in a manner that the user operates the mouse 57 or the keyboard 56 to move a cursor (not illustrated) on the display 58 to the partial area to be designated, and performs clicking operation of the mouse 57 (or pressing-down of an enter key of the keyboard 56).

Meanwhile, the CPU 51 of the present step reads, as a history of the extraction target candidate, a time lapse movie image of the extraction target candidate from the storage memory 53, and writes the time lapse movie image into an area for movie image display of the working memory 54. Further, the CPU 51 starts displaying a still image of a predetermined frame (the latest frame, for example) of the time lapse movie image, as a sample image, on a predetermined area on the display 58, as indicated by a reference numeral 58*a* in FIG. 6.

Further, the CPU 51 displays a play button 58*a*', in the vicinity of the sample image 58*a* (the sample image of the time lapse movie image) on the display 58. The play button 58*a*' is a button with which the user inputs an instruction of playing the time lapse movie image, into the computer 50.

Further, the CPU 51 of the present step creates a container image of the reserve container 40, and displays the image on a remaining area of the display 58, as indicated by a reference numeral 58*e* in FIG. 6. The container image 58*e* is an image schematically representing an arrangement of the plurality of reservoirs of the reserve container 40.

Further, the CPU 51 highlights a reservoir disposed at the aforementioned reserve position 40*a*, among the plurality of reservoirs that form the container image 58*e*, as a current ejection target candidate. Hereinafter, it is set that the highlighting of the reservoir is performed by thickening a contour line of the reservoir, as illustrated in FIG. 6.

Note that when the user selects a reservoir which is not highlighted on the container image 58*e*, it is possible to cancel the designation of the ejection target candidate at the present moment, and to designate the selected reservoir as a new ejection target candidate.

Note that the designation of the reservoir by the user is conducted in a manner that the user operates the mouse 57 or the keyboard 56 to move the cursor (not illustrated) on the display 58 to the reservoir to be designated, and performs clicking operation of the mouse 57 (or pressing-down of the enter key of the keyboard 56).

Step S23: The CPU 51 judges whether or not a new designation of the extraction target candidate is made, in which when the new designation is made, the process proceeds to step S24, and when the new designation is not made, the process proceeds to step S26.

Step S24: The CPU 51 calculates, based on container coordinates of the newly designated extraction target candidate and coordinates of the observation stage 11 at the present moment, target coordinates of the observation stage 11 for disposing the newly designated extraction target candidate on the optical axis, and gives an instruction of driving the observation stage 11 together with the target coordinates, to the controlling circuit 52. The controlling circuit 52 drives the observation stage 11 to make actual coordinates of the observation stage 11 coincide with the target coordinates, to thereby dispose a center of the newly designated extraction target candidate on the optical axis.

Step S25: The CPU 51 updates the tiling fluorescence image 58*d* on the display 58, the time lapse movie image on the area for movie image display, and the sample image 58*a* on the display 58, in the following manner.

The CPU 51 cancels the highlighting at the present moment on the tiling fluorescence image 58*d*, and starts highlighting of the extraction target candidate newly designated on the tiling fluorescence image 58.

Further, the CPU 51 displaces, in accordance with the displacement of the observation stage 11 in step S24, the superimposing position of the tiling fluorescence image 58*d* on the macro live image 58*c*, to thereby make a center of the container in the tiling fluorescence image 58*d* coincide with a center of the container in the macro live image 58*c*.

Further, the CPU 51 reads the time lapse movie image of the newly designated extraction target candidate from the storage memory 53, and overwrites the time lapse movie image into the area for movie image display of the working memory 54. Further, the CPU 51 starts displaying a predetermined frame (the latest frame, for example) of the time lapse movie image, instead of the sample image 58*a* which is being displayed.

Figure 8:
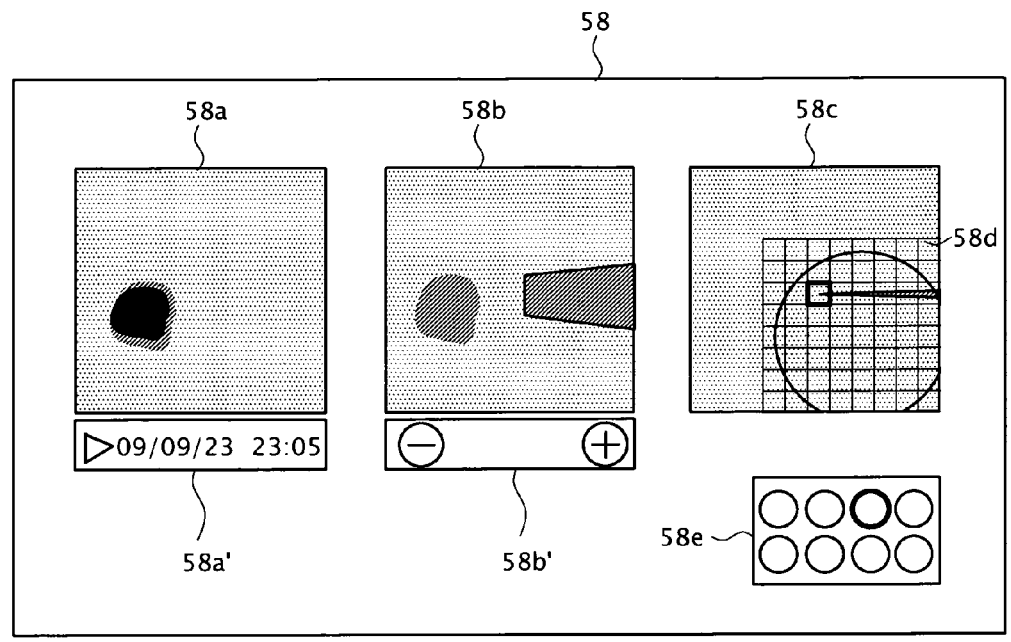
FIG. 8 is a diagram illustrating an updated display screen of the display 58.

Note that FIG. 8 illustrates an example of screen updated by the present step. A partial area separated from the center of the container is designated as the extraction target candidate on the macro live image 58*c* illustrated in FIG. 8, the micro live image 58*b* shows a micro dark-field image of the extraction target candidate, and the sample image 58*a* shows a history of the extraction target candidate (a state at a time of the latest observation, in this case).

Step S26: The CPU 51 judges whether or not a new designation of the ejection target candidate is made, in which when the new designation is made, the process proceeds to step S27, and when the new designation is not made, the process proceeds to step S29.

Step S27: The CPU 51 calculates, based on a number of the newly designated ejection target candidate and coordinates of the reserve stage 60 at the present moment, target coordinates of the reserve stage 60 for disposing the newly designated ejection target candidate at the aforementioned reserve position 40a, and gives an instruction of driving the reserve stage 60 together with the target coordinates, to the controlling circuit 52. The controlling circuit 52 drives the reserve stage 60 to make actual coordinates of the reserve stage 60 coincide with the target coordinates, to thereby dispose the newly designated ejection target candidate at the reserve position 40a.

Step S28: The CPU 51 cancels the highlighting at the present moment of the container image 58e, and starts highlighting of the newly designated ejection target candidate. Note that a reference numeral 58e in FIG. 8 indicates an example of the container image 58e updated by the present step.

Step S29: The CPU 51 judges whether or not the instruction of changing the observation magnification is input, in which when the instruction is input, the process proceeds to step S30, and when the instruction is not input, the process proceeds to step S31.

Step S30: The CPU 51 instructs the controlling circuit 52 to change the observation magnification. The controlling circuit 52 drives the revolver 18d to switch the observation magnification of the micro imaging optical system 18.

Step S31: The CPU 51 judges whether or not the instruction of playing the time lapse movie image is input, in which when the instruction is input, the process proceeds to step S32, and when the instruction is not input, the process proceeds to step S33.

Figure 9:
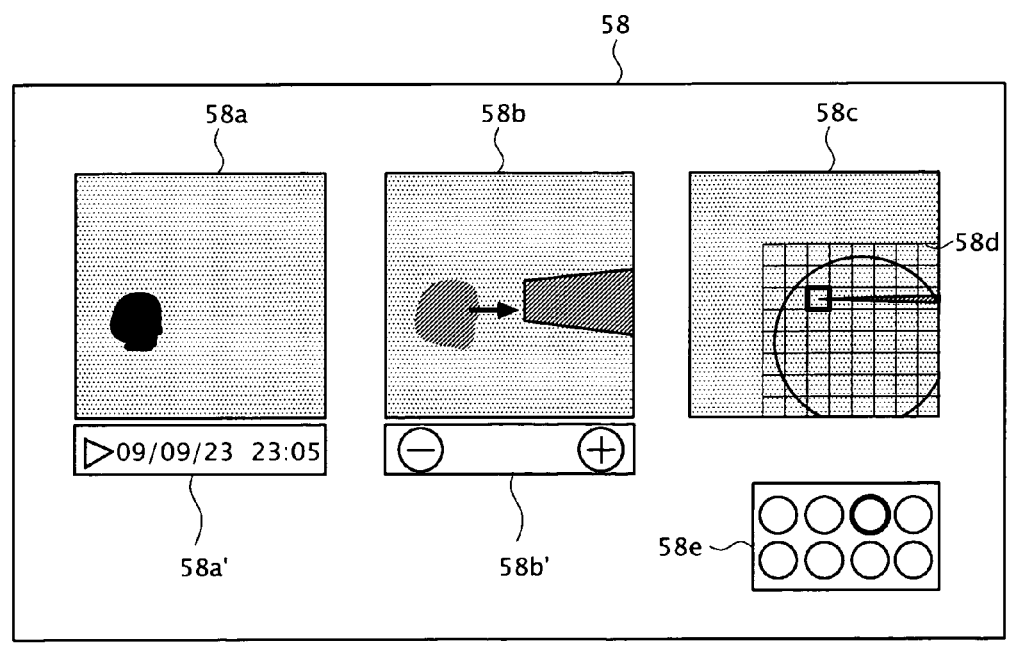
FIG. 9 is a diagram illustrating a display screen of the display 58 during an operation of a manipulator.

Step S32: The CPU 51 displays (plays and displays) the time lapse movie image written on the area for movie image display, instead of the sample image 58a. Through the play and display, the user can observe a growing process (a variation with time of an amount of fluorescence and the like) of the cell colony existed in the extraction target candidate, and can accurately judge whether or not the cell colony is an iPS cell colony. When the user judges that the cell colony is the iPS cell colony, it is only required to operate the stage controller 12 while looking the micro live image 58b, to thereby make the iPS cell colony to be slowly approximated to the side of the tip of the syringe 22, as indicated by an arrow mark in FIG. 9.

Step S33: The CPU 51 judges, via the controlling circuit 52, whether or not the stage controller 12 is operated, in which when the operation is made, the process proceeds to step S34, and when the operation is not made, the process proceeds to step S35.

Step S34: The CPU 51 gives a driving signal generated by the stage controller 12 to the observation stage 11 via the controlling circuit 52. Accordingly, the observation stage 11 is driven as the user desires. Note that in this case, it is assumed that a moving range of the observation stage 11 is limited to a very small range, which is small enough to prevent the tip of the syringe 22 from being separated from the extraction target candidate in the incubation container 30. When the user judges that the iPS cell colony sufficiently approaches the tip of the syringe 22 on the micro live image 58b, he/she stops the driving of the observation stage 11, and starts the operation of the manipulator controller 21.

Step S35: The CPU 51 judges, via the controlling circuit 52, whether or not the manipulator controller 21 is operated, in which when the operation is made, the process proceeds to step S36, and when the operation is not made, the process proceeds to step S39.

Step S36: The CPU 51 gives a driving signal generated by the manipulator controller 21 to the manipulator 20 via the controlling circuit 52. Accordingly, the manipulator 20 is driven as the user desires. For example, when the user makes the syringe 22 shift downward, the tip of the syringe 22 is brought into contact with the iPS cell colony, the iPS cell colony is sucked into the syringe 22, and after the syringe 22 is set to be in the separating mode, the iPS cell colony is ejected to the outside from the syringe 22.

Step S37: The CPU 51 judges, based on the driving signal generated by the manipulator controller 21, whether or not the fluid is ejected from the syringe 22 in the separating mode (whether or not the picking is completed), in which when the fluid is ejected (when the picking is completed), the process proceeds to step S38, and when the fluid is not ejected (when the picking is not completed), the process proceeds to step S39.

Figure 10:
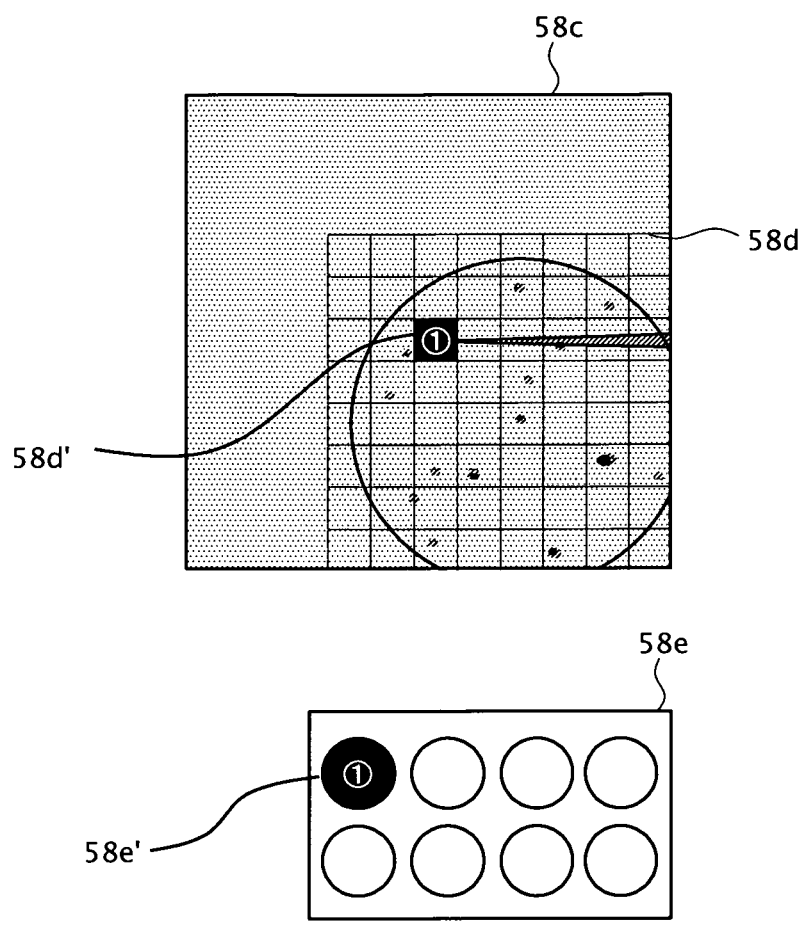
FIG. 10 is a diagram explaining an extraction completion mark and an ejection completion mark.

Step S38: As illustrated in FIG. 10, the CPU 51 displays the extraction target candidate on the tiling fluorescence image 58d in a more highlighted manner (performs reverse display, for example), and gives an extraction completion mark 58d' to the extraction target candidate. Further, the CPU 51 displays the ejection target candidate on the container image 58e in a more highlighted manner (performs reverse display, for example), and gives an ejection completion mark 58e' to the ejection target candidate.

Here, in order to clarify the correspondence between the extraction target candidate which is already extracted and the ejection target candidate in which the ejection is already made, the CPU 51 provides relevance between the extraction completion mark 58d' and the ejection completion mark 58e'. For example, the CPU 51 recognizes the number of times of picking with respect to the incubation container 30, based on the number of times of execution of the present step up to the present moment, and the like, and applies a number representing the number of times, to both of the extraction completion mark 58d' and the ejection completion mark 58e'. Therefore, the user can intuitively know that the cell of Which partial area is reserved in which reservoir, on the display 58.

Note that the extraction completion mark 58d' given to the tiling fluorescence image 58d is kept given to the same partial area on the tiling fluorescence image 58d, even if the superimposing position of the tiling fluorescence image 58d on the macro live image 58c is changed thereafter. Therefore, the user can avoid a mistake of designating again the partial area which is already extracted as the extraction target candidate, a mistake of reserving a cell extracted from a different cell colony in the same reservoir, and the like.

Note that when, after displaying the extraction completion mark 58d', the user selects a partial area to which the extraction completion mark 58d' is not given on the tiling fluorescence image 58d, the partial area can be designated as a new extraction target candidate.

Further, when, after displaying the ejection completion mark 58e', the user selects a reservoir to which the ejection completion mark 58e' is not given on the container image 58e, the reservoir can be designated as a new ejection target candidate.

Step S39: The CPU 51 judges whether or not the termination instruction is input by the user, in which when the instruction is not input, the process returns to step S23, and when the instruction is input, the flow is terminated. Therefore, the user can repeatedly perform a picking of cell colonies until the ejection completion marks 58e' are given to all of the reservoirs of the container image 58e.

As described above, the present system includes the macro imaging optical system 14 and the micro imaging optical system 18 that observe the incubation container 30 from mutually opposite sides, and the oblique illuminating optical system 15 that illuminates the incubation container 30 from the diagonal direction, as illustrated in FIG. 1, so that it is possible to simultaneously observe a brief state of the entire incubation container 30 (the macro dark-field image) and a detailed state of a part of the incubation container 30 (the micro dark-field image).

Furthermore, since the computer 50 of the present system simultaneously displays, on the display 58, both of the live image of the macro dark-field image (the macro live image 58c) and the live image of the micro dark-field image (the micro live image 58b) arranged side by side, the user does not have to switch the objective lens between when searching for the cell colony which seems like the iPS cell colony among the plurality of cell colonies in the incubation container 30, and when observing the cell colony in detail, and the user is only required to transfer his/her gaze on the display 58 between the macro live image 58c and the micro live image 58b.

Further, the computer 50 of the present system previously stores the time lapse movie image of each partial area of the incubation container 30 in the storage memory 53. Further, the computer 50 reads the time lapse movie image of the partial area (the extraction target candidate) positioned on the optical axis of the micro imaging optical system 18 from the storage memory 53, and displays it, together with the micro live image 58b, on the display 58, so that the user can simultaneously check the detailed state of the cell colony and the history of the cell colony.

Further, since the computer 50 of the present system performs superimposing display of the latest tiling fluorescence image 58d of the incubation container 30 on the macro live image 58c, the user can simultaneously observe the current state (the texture, the size, and the like) of the plurality of cell colonies dotted in the incubation container 30, and the recent degree of fluorescence of those cell colonies.

Further, the computer 50 of the present system drives the observation stage 11 in accordance with the designation of the extraction target candidate made by the user, and automatically disposes the extraction target candidate on the optical axis (step S24), so that it is possible to minimize user's time and labor required for operating the stage controller 12.

Further, the computer 50 of the present system judges whether or not the fluid is ejected from the syringe 22 in the separating mode, via the manipulator controller 21, and when the fluid is ejected, the computer 50 highlights (reverse display) the extraction target candidate on the tiling fluorescence image 58d, so that the user can intuitively know that the cell of which partial area is already extracted, on the tiling fluorescence image 58d.

Second Embodiment

Hereinafter, an embodiment of another cell observing system will be described as an embodiment of the present invention, with reference to FIG. 11 to FIG. 15. Note that in a second embodiment, members denoted by the same reference numerals as those of the first embodiment are the same members as those of the first embodiment including the configurations and the operations, so that explanation thereof will be omitted.

Figure 11:
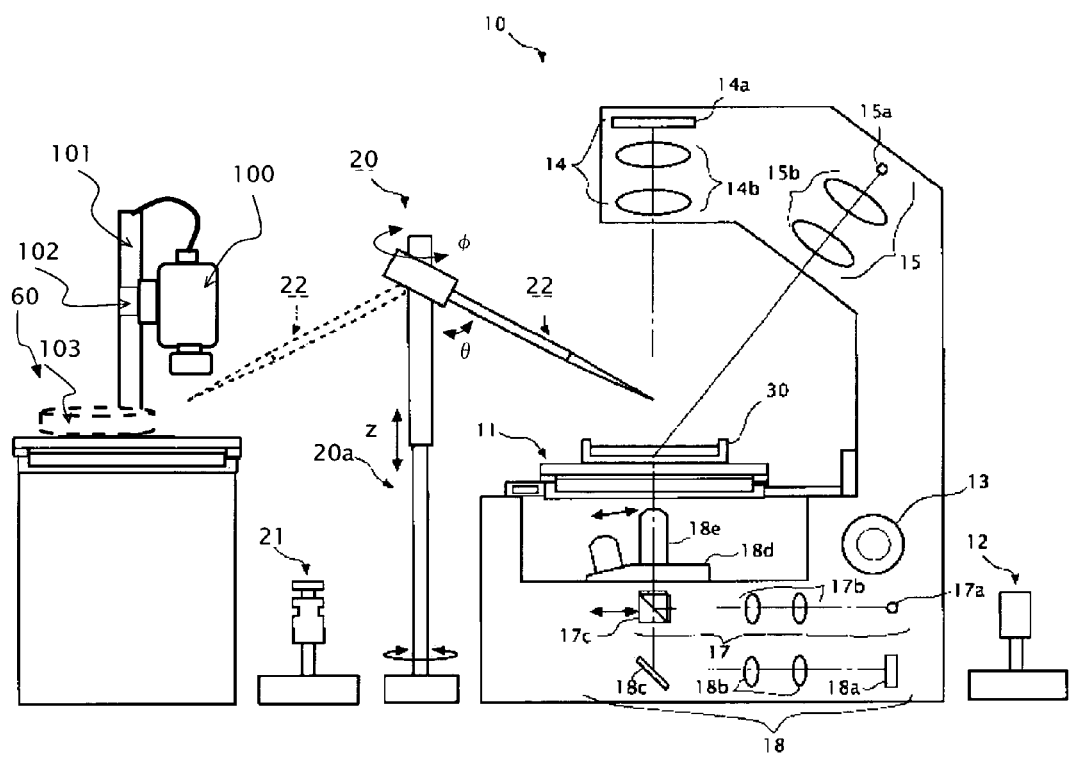
FIG. 11 is a configuration diagram of a system of a second embodiment (mainly a mechanical part).
Figure 12:
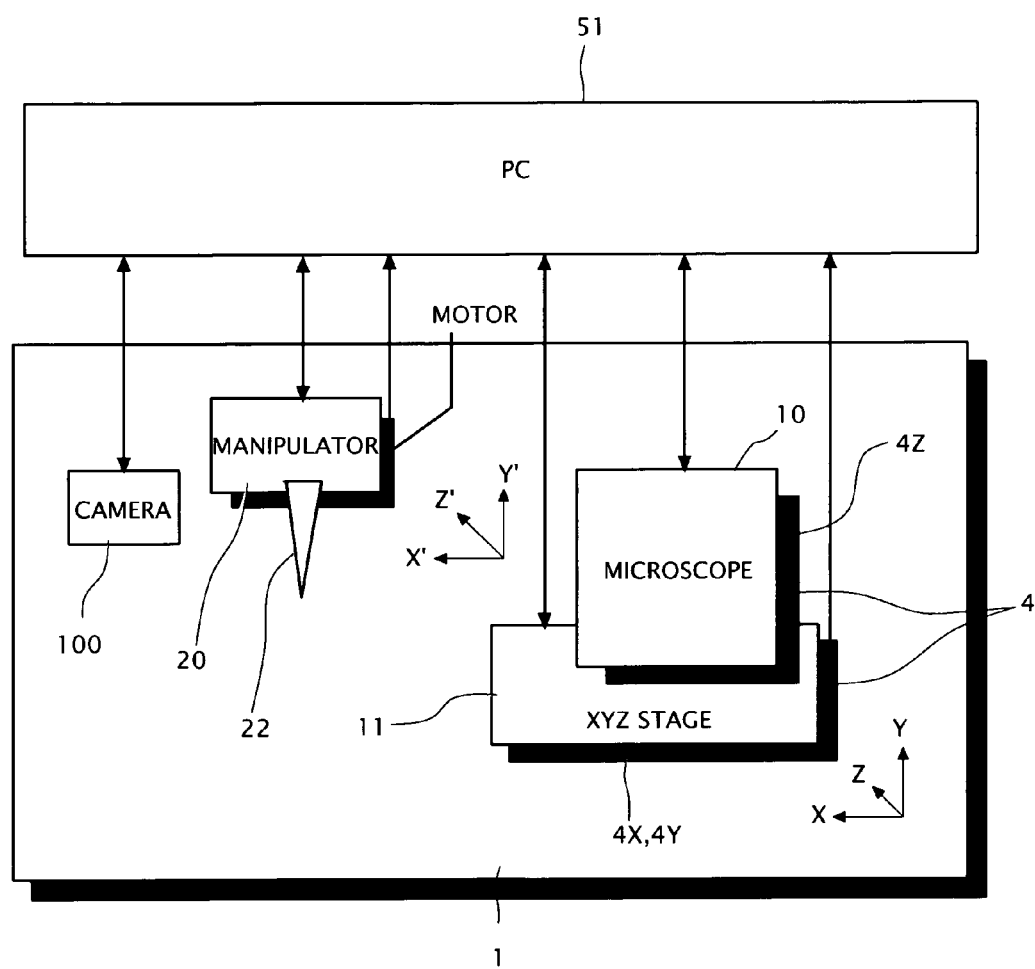
FIG. 12 is a configuration diagram of the system of the second embodiment (mainly a circuit part).

FIG. 11 and FIG. 12 are configuration diagrams of the present system. A characteristic configuration in the second embodiment is a configuration in which the cell observing system is automated, which is, concretely, a configuration in which the manipulator 20 automatically controls the syringe 22 based on a wide-area image (an image of the entire incubation container) obtained by the macro imaging optical system 14, and a partial-area image (an image of a focused cell) obtained by the micro imaging optical system 18.

The inverted microscope 10, the manipulator 20, and the reserve stage 60 are disposed on the same base. The change in the observing position in the incubation container 30 is conducted by moving the incubation container 30 in the XY plane by using the observation stage 11. As illustrated in FIG. 12, the observation stage 11 is provided with an observing position detecting unit 4 formed of an X-direction position detecting encoder 4X and a Y-direction position detecting encoder 4Y, and by detecting XY coordinates of the observation stage 11, observing position coordinates (corresponding to a coordinate system of cell) (X, Y) in the incubation container 30 are detected. Further, regarding a Z coordinate at the observing position in the incubation container 30, by detecting a vertical motion of the objective lens 18e made by the focus knob 13, using an observing position detecting unit 4 formed of a Z-direction position detecting encoder 4Z, the observing position coordinate Z in the incubation container 30 is detected. Accordingly, coordinate data (X, Y, Z) at the observing position in the incubation container 30 is detected, and the coordinate data is registered in a memory of the CPU 51 (a personal computer PC or the like, which is described as PC, hereinafter) being a controlling device.

The manipulator 20 has a motor that changes a rotation angle ϕ of the syringe 22 (manipulation needle), a motor that changes a swing angle θ of the syringe 22, and a motor that changes a movement amount Z of the syringe 22 in the optical axis direction.

A coordinate system of the manipulator 20 is detected by a manipulator coordinate detecting unit formed of position detecting encoders in the X' direction, Y' direction, and Z' direction disposed in the manipulator 20. Further, coordinates of the tip of the syringe 22 fixed to the manipulator 20 are registered in the memory of the PC 51 as coordinate data (X', Y', Z').

Further, as illustrated in FIG. 11, in the vicinity of the manipulator 20, there is disposed a needle tip position detecting unit 100 that detects the tip of the syringe 22 fixed to the manipulator 20. The needle tip position detecting unit 100 is a camera using a low-power imaging lens and imaging device (a CCD camera or the like, for example) (described as low-power camera 100, hereinafter), and as the lens of the low-power camera 100, it is desired to use a lens with a numerical aperture of 0.2 or more and a field number of 1.5 mm or more, for performing positioning of the tip of the syringe 22 at a set position in an observation field of view of the objective lens 18e, with high accuracy. Further, it is also possible that the needle tip position detecting unit 100 is formed of, not the camera, but a simple optical sensor that detects whether or not the needle tip reaches predetermined position coordinates.

Coordinate data at the set position in the field of view of the objective lens 18e and coordinate data of the tip of the syringe 22, and a set position in a field of view of the low-power camera 100 are relatively associated via the PC 51. As a result of this, the tip of the syringe 22 is set at the set position in the field of view of the low-power camera 100, and thereafter, it is driven by the manipulator 20 via the controlling unit of the PC 51 to be positioned at the set position in the field of view of the objective lens 18e. As described above, calibration of the coordinate position of the tip of the syringe 22 is conducted. Note that at the time of performing the calibration, the incubation container 30 is not placed on the observation stage 11. Further, when a plurality of objective lenses with various magnifications are used, the calibration is conducted with respect to each of the objective lenses.

In like manner, coordinate data at a set position in a field of view of the macro imaging optical system 14 and the coordinate data of the tip of the syringe 22, and the set position in the field of view of the low-power camera 100 are relatively associated via the PC 51. As a result of this, the tip of the syringe 22 is set at the set position in the field of view of the low-power camera 100, and thereafter, it is driven by the manipulator 20 via the controlling unit of the PC 51 to be positioned at the set position in the field of view of the macro imaging optical system 14.

After an initial setting operation to be described below, the manipulator 20 is controlled by the controlling unit provided in the PC 51, resulting in that the tip of the syringe 22 is moved from the set position in the field of view of the low-power camera 100 to the set position in the observation field of view of the objective lens 18*e*, and set at a predetermined position of the incubation container 30. Note that the set position is located in the vicinity of a center of the field of view, and is set as an observing position suitable for starting an operation of experiment.

(Initial Setting Operation)

Next, a positioning process of the tip of the syringe 22 will be described while referring to a flow chart executed by the PC 51 illustrated in FIG. 13.

First, an initial setting of home position of the coordinate system (X, Y, Z) of the inverted microscope 10 is conducted (S1).

Figure 13:
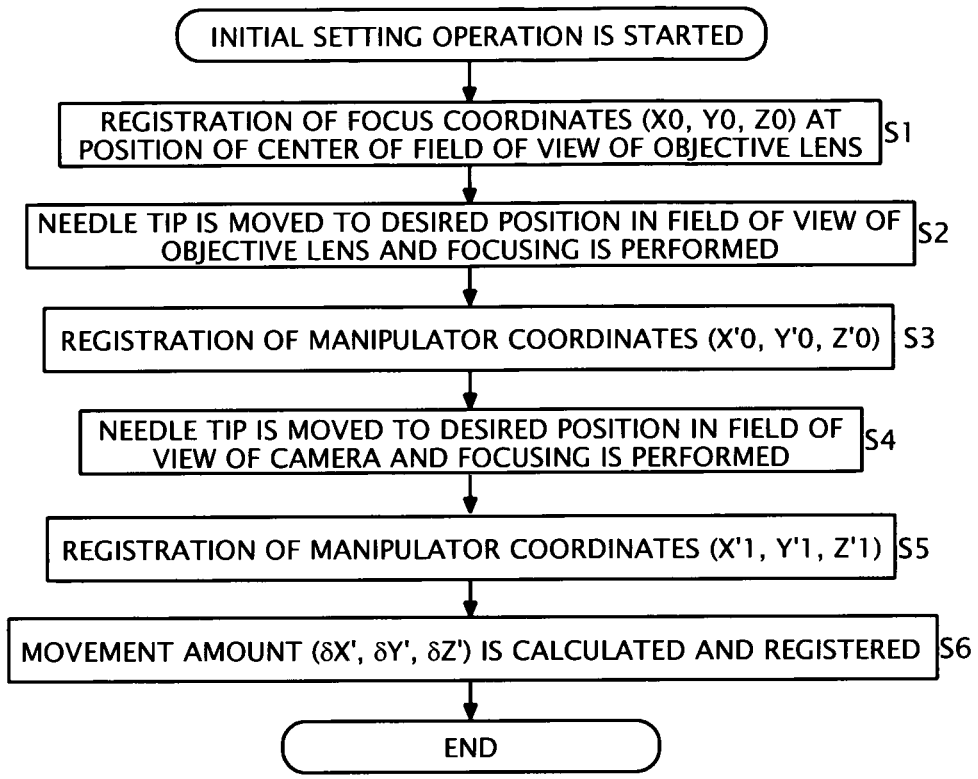
FIG. 13 is a flow chart of an initial setting operation.

As illustrated in FIG. 13, focusing of the objective lens 18*e* of the inverted microscope 10 is performed. In the focusing, a bead with a diameter of several pal such as polystyrene placed on a cover glass is used, and focusing is performed on the bead in the center of the field of view of the objective lens 18*e*. Concretely, an operator moves the bead to a position of the center of the field of view of the objective lens 18*e* (utilizing cross hairs for shooting in the optical system, or the like), and operates the observation stage 11 and the focus knob 13 to perform focusing on the bead. Under this state, the observing position detecting units 4 (4X, 4Y, 4Z) detecting the XY movements of the observation stage 11 and the vertical motion of the objective lens 18*e* transmit detected coordinate data (X0, Y0, Z0) to the PC 51, and the PC 51 registers the coordinate data (X0, Y0, Z0) in the memory as home position data. Note that the focus knob 13 that moves the observation stage 11 and the objective lens 18*e* may be electrically operated or manually operated.

Next, explanation will be made on the initial setting operation in which a relative positional relation between the tip position of the syringe 22 in the field of view of the objective lens 18*e* and the tip position of the syringe 22 in the field of view of the low-power camera 100 is determined by the coordinate system (X', Y', Z') of the manipulator 20.

Through this initial setting operation, a correlation between the tip position of the syringe 22 at the set position in the field of view of the low-power camera 100 (the tip position is often set at the position of the center of the field of view) and the tip position of the syringe 22 at the set position in the observation field of view of the high-power (40-power, for example) objective lens 18*e* (the tip position is often set at the center of the field of view), is registered in advance in the memory of the PC 51.

Concretely, when the operator operates the manipulator 20 to move the tip of the syringe 22 to the predetermined set position in the field of view of the low-power camera 100, coordinate data of the manipulator 20 at this time is registered in the PC 51. Further, when the tip of the syringe 22 is moved to the predetermined set position in the field of view of the objective lens 18*e*, coordinate data of the manipulator 20 at this time is registered in the PC 51. Based on these two pieces of coordinate data, the PC 51 recognizes the correlation between the set position in the field of view of the low-power camera 100 and the set position in the field of view of the objective lens 18*e*.

Description will be made further concretely. The operator drives the manipulator 20 in each direction of X', Y', and Z', to move the tip of the syringe 22 to the set position in the field of view of the objective lens 18*e*, and focuses the objective lens 18*e* on the tip of the syringe 22 (S2).

At this time, a manipulator coordinate detecting unit 22 transmits detected coordinate data (X'0, Y'0, Z'0) of the manipulator 20 to the PC 51, and the PC 51 registers the data in the memory (S3). Note that as a method of registration, it is possible to employ a method in which a manually-operated switch is used, or a method in which, when there is an automatic focusing device for detecting coordinates of the tip of the syringe 22 set at the set position in the field of view of the objective lens 18*e*, the registration is made based on a focusing signal transmitted by the automatic focusing device.

Next, the operator drives the manipulator 20 in each direction of X', Y', and Z', to move the tip of the syringe 22 to the set position in the field of view of the low-power camera 100, and focuses the low-power camera 100 on the tip of the syringe 22 (54).

At this time, the manipulator coordinate detecting unit 22 transmits detected coordinate data (X'1, Y'1, Z'1) of the manipulator 20 to the PC 51, and the PC 51 registers the data in the memory (S5). Note that as a method of registration, it is possible to employ a method in which a manually-operated switch is used, or a method in which, when there is an automatic focusing device in the low-power camera 100, the registration is made based on a focusing signal transmitted by the automatic focusing device.

By using the above two pieces of coordinate data of the manipulator 20, the PC 51 calculates a movement amount ($\phi$, $\theta$, Z) of the tip of the syringe 22.

Regarding movement amount data of the tip from the set position in the field of view of the low-power camera 100 to the set position in the field of view of the objective lens 18*e*, pieces of difference data among respective coordinates of the manipulator 20, namely, $\delta X'=X'1-X'0$, $\delta Y'=Y'1-Y'0$, and $\delta Z'=Z'1-Z'0$, are respectively calculated, and are registered, as the movement amount data ($\delta X'$, $\delta Y'$, $\delta Z'$), in the memory of the PC 51 (S6). This is the end of the initial setting operation.

As described above, the initial setting operation, namely, the calibration is terminated.

Accordingly, when the tip of the syringe 22 is set at the set position in the field of view of the low-power camera 100, the manipulator 20 is driven by the controlling unit of the PC 51, and the tip of the syringe 22 is automatically set at the set position in the field of view of the objective lens 18*e*.

(Explanation of Automatic Control of Manipulator 20 Based on Automatic Recognition of Cell Image)

Figure 14:
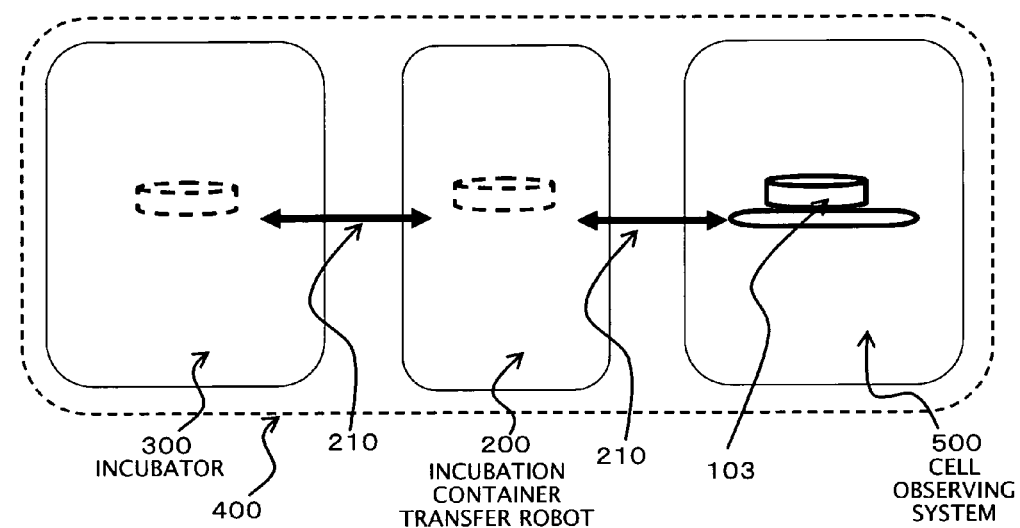
FIG. 14 is a configuration diagram of a cell production system.

FIG. 14 is a configuration diagram of a cell production system. In the configuration of the cell production system in FIG. 14, an incubator 300 and a cell observing system 500 (the system of the first embodiment or the second embodiment) are connected by an incubation container transfer robot 200. A space 400 in which the cell production system exists is managed to be put under a certain incubation environment. Note that the incubation environment mentioned here includes conditions of temperature, humidity, carbon dioxide and the like.

In this cell production system, an incubation container 103 in which cells are incubated is subjected to macro observation by the macro imaging optical system 14 to obtain a wide-area image, a position of cell is specified from the wide-area image and the cell is subjected to micro observation by the micro imaging optical system 18, to thereby obtain a partial-area image in the wide-area image. Thereafter, a state of the cell is judged based on the partial-area image, and the cell whose state is judged as good (good cell) is picked up from the incubation container 103. The picking is performed by controlling the tip of the syringe 22 based on the wide-area image and the partial-area image. Further, the cell picked up by the syringe 22 is seeded in a new incubation container 103, and thereafter, the new incubation container 103 is transferred to the incubator 300. The seeded cell is incubated for a certain period of time in the incubator. By repeating the routine, it is possible to incubate the good cell, and to increase the number of the good cell.

The control of picking performed by the syringe 22 is conducted in the following manner. Specifically, an XY coordinate position of the tip of the syringe 22 is made to coincide with an XY coordinate position of the cell based on the wide-area image obtained by the macro imaging optical system, and the tip is driven toward an XYZ coordinate position of the cell based on the partial-area image obtained by the micro imaging optical system, to thereby perform a picking of the cell using the syringe 22. Further concrete description is as follows.

Figure 15:
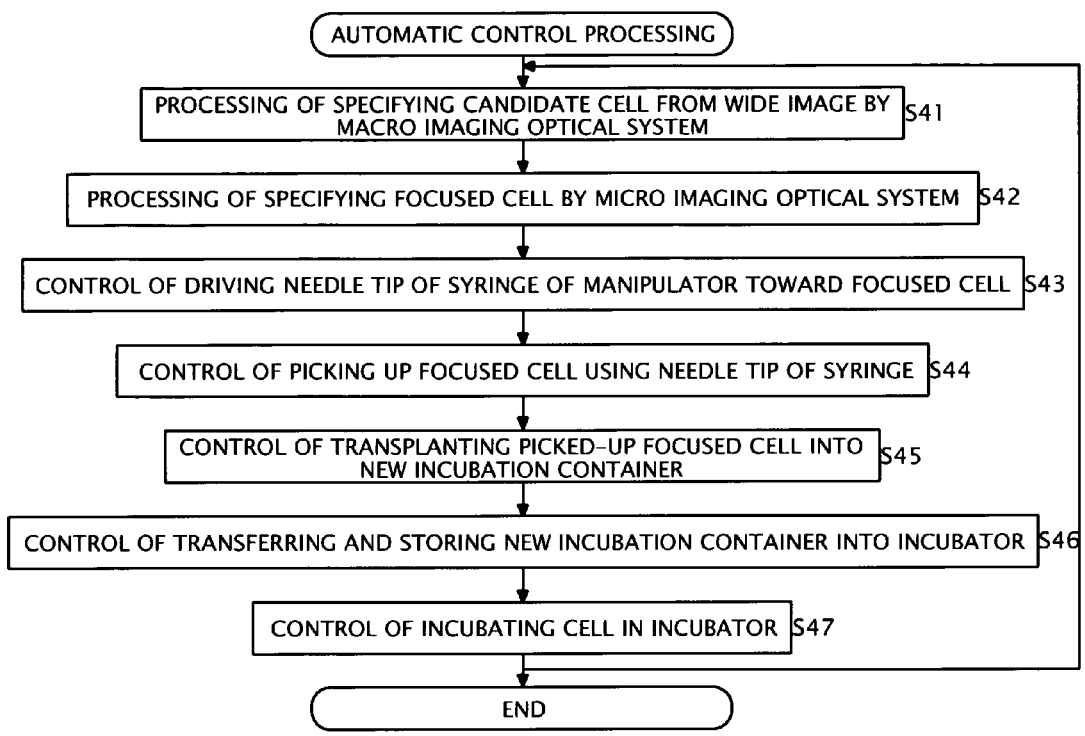
FIG. 15 is a flow chart of the cell production system.

As illustrated in FIG. 15, the computer 50 in FIG. 2 executes a predetermined program to carry out a control of automatically controlling the manipulator 20 based on cell images obtained by the macro imaging optical system 14 and the micro imaging optical system 18, to pick up a focused cell, and incubating and proliferating the cell. The processing of the computer 50 will be described based on FIG. 15.

Step 41: Cell images of wide area obtained by the macro imaging optical system 14 are stored in the storage memory 53 in FIG. 2. Based on the stored cell images (a plurality of cell images obtained through time lapse shooting), the CPU 51 performs processing of specifying an iPS cell colony.

The processing of specifying the iPS cell colony includes processing of detecting a coordinate position (XY coordinate value) of the focused cell based on the wide-area image, and processing of judging a noise component which is not the focused cell. For example, it is possible to read the fluorescence to specify the iPS cell colony as explained in the first embodiment, or, when the detection is made in a noninvasive manner, it is also possible to specify the iPS cell colony from morphological information based on a phase-contrast observation image.

The focused cell to be a candidate is specified based on the cell image of wide area. Specifically, cells in the incubation container include an air bubble, a dead cell, a colony cell in an early stage before the cell colony is formed, and so on, to be the noises. In order to remove these noise components, the morphological information of each of the cells scattered in the incubation container is extracted, based on a bright-field observation image (a transmission observation image, a phase-contrast observation image, an observation image obtained through oblique illumination, or the like, for example) obtained by the macro imaging optical system 14. Based on the extracted morphological information of each of the cells, which is, for example, information regarding an area of the cell, information regarding a length of a long side of the cell, information regarding a circular degree of the cell, or the like, a cell which does not satisfy predetermined conditions is excluded from a candidate as a noise. If it is configured as above, it is possible to set only the iPS cell colony with good state, to a candidate cell.

Conversely, it is also possible to specify the cell to be the noise as the candidate cell, by performing the above-described processing based on the cell image of wide area. However, in that case, the subsequent processing corresponds to processing in which the cell to be the noise is picked up to leave only a good cell. Accordingly, in that case, the incubation can be continued without using a new incubation container.

Step 42: Processing in which the focused cell (iPS cell colony) is specified from the candidate cell specified in step 41, is carried out.

A coordinate position (XY coordinate value) of the focused cell is determined based on the wide-area image, the observation stage 11 is driven based on the coordinate position, and an image of the focused cell is obtained by the micro imaging optical system 18 (when there exist a plurality of focused cells, images of the respective focused cells are obtained). Further, processing in which a culturing state of the focused cell is judged based on the obtained partial-area image (the image of the focused cell), is conducted. For example, it is possible to read the fluorescence to specify the iPS cell colony as explained in the first embodiment, or, when the detection is made in a noninvasive manner, it is also possible to specify the iPS cell colony from the morphological information based on the phase-contrast observation image.

Note that when the morphological information of the iPS cell colony is used, a high-definition phase-contrast observation image obtained by the micro imaging optical system 18 is used. As a concrete method of specifying the iPS cell colony, there is a method, for example, in which well-known contour line extraction processing (binarization processing or differential processing, for example) for iPS cell colony is performed on the phase-contrast observation image, and when a variance value of brightness intensity of cell image within the contour line extracted through the processing is recognized to be less than a predetermined variance value (when a cell colony is recognized as a cell colony with uniformity), an iPS cell colony within the contour line is regarded as a good iPS cell colony.

Accordingly, the good iPS cell colony in the incubation container is specified. A processing timing of such steps 41 and 42 is previously set by the observing schedule, and, for example, steps S41 and 42 are executed at predetermined time intervals during when the time lapse observation shooting is performed, or steps S41 and 42 are executed after the shooting is performed a predetermined number of times. The processing timing is experientially set based on the incubation time of the iPS cell colony and the like.

Step 43: When the iPS cell colony being the focused cell is detected, the manipulator 20 is automatically controlled based on the macro image 58*d* and the micro image 58*b*, as illustrated in FIG. 6. Concretely, the dark-field image 22' of the syringe captured on the macro image is first detected based on image information of the macro image 58*d*, and a coordinate system of the manipulator 20 is calculated by the manipulator coordinate detecting unit 22. Further, there is performed a control in which a coordinate position of the tip of the syringe is set at a coordinate position (XY coordinate value) of the focused cell determined in step 41. Thereafter, the syringe is driven in the Z direction from the coordinate position (XY coordinate value) of the focused cell. When the tip of the syringe enters a predetermined range from the position of the focused cell, the micro imaging optical system can capture the tip, and accordingly, a minute control of the manipulator 20 is performed based on image information of the micro image 58*b*. The micro image 58*b* has the image information with higher definition than that of the macro image 58d, so that a coordinate position (XYZ coordinate value) of the focused cell and a coordinate position (XYZ coordinate value) of the tip of the syringe can be controlled in a micrometer unit.

Step 44: The tip of the syringe approaches the focused cell, and the focused cell is picked up (sucked into the syringe).

Step 45: The manipulator 20 is automatically controlled, and the picked-up focused cell is seeded in a new incubation container 103 in FIG. 11 to be transplanted.

Step 46: The transfer robot 200 in FIG. 15 transfers the new incubation container 103 to the incubator 300 from the cell observing system 500 in FIG. 11. The transfer robot 200 grips the new incubation container 103 with its articulated transfer arm 210, and transfers the incubation container 103 from an opening of the incubator 300 into a room in which the environment is maintained.

Step 47: The incubation container 103 transferred to the incubator 300 is kept in an environment optimum for incubating the iPS cell colony, and the incubation is conducted for a predetermined period of time. An imaging device (a CCD camera or the like) provided in the incubator 300 performs time lapse shooting of the incubation container 103, to obtain images of the iPS cell colony. Based on the images, a culturing state of the iPS cell colony is sequentially analyzed.

The iPS cell colony incubated in the incubator 300 is again transferred to the cell observing system 500 by the incubation container transfer robot 200, after the elapse of predetermined period of time. Subsequently, the flow chart in FIG. 15 is repeatedly executed as described above, in which the culturing state of the cell is analyzed and the cell incubation is repeatedly carried out. Accordingly, it is possible to proliferate only the good iPS cell colony.

Supplement to Embodiments

Note that in the system of each of the aforementioned embodiments, the number of partial areas which can be simultaneously designated as the extraction target candidates is set as one, but, the number may also be plural. In such a case, the computer 50 is only required to make the user newly designate one of a plurality of extraction target candidates in a state of being designated, and to drive the observation stage 11 so that the newly designated extraction target candidate is disposed on the optical axis.

Further, in the system of each of the aforementioned embodiments, a rough adjustment of the observation stage 11 is automatically conducted, and a fine adjustment of the observation stage 11 is manually conducted (by the stage controller 12), but, all of the adjustment of the observation stage 11 may also be manually conducted (by the stage controller 12).

In such a case, when the user designates the extraction target candidate on the tiling fluorescence image 58d, only the superimposing position of the tiling fluorescence mage 58d is shifted in a state where the contents of the macro live image 58c do not change, so that the user is only required to look the macro live image 58c and the tiling fluorescence image 58d, and to manually drive the observation stage 11 so that a dark-field image of cell colony group in the macro live image 58c is superimposed on a fluorescence image of cell colony group in the tiling fluorescence image 58d.

Further, in the system of each of the aforementioned embodiments, one oblique illuminating optical system 15 is shared by the macro imaging optical system 14 and the micro imaging optical system 18, but, it is also possible to use an oblique illuminating optical system dedicated to the macro imaging optical system 14, and an oblique illuminating optical system dedicated to the micro imaging optical system 18. Note that in such a case, it is also possible to set at least one of the oblique illuminating optical system for the macro imaging optical system 14 and the oblique illuminating optical system for the micro imaging optical system 18, as a dark-field epi-illumination optical system.

Further, in the system of the present embodiment, the macro imaging optical system 14 and the micro imaging optical system 18 are disposed to face each other with the observation stage 11 being located therebetween, but, the configuration is not limited to that, and, for example, it is also possible that both of the imaging optical systems are disposed on one side of the observation stage 11. Concretely, it is only required that a micro imaging optical system is disposed at the position of the macro imaging optical system 14 illustrated in FIG. 1, a macro imaging optical system is disposed at the position of the oblique illuminating optical system 15, and a transmission illuminating optical system is disposed at the position of the micro imaging optical system 18.

Further, in the system of the present embodiment, the macro imaging optical system that obtains the wide-area image of the incubation container is formed of a low-resolution CCD sensor, and the micro imaging optical system that obtains the partial-area image in the wide-area image of the incubation container is formed of a high-resolution CCD sensor. Accordingly, in the micro imaging optical system, by performing trimming of a captured image, it is possible to obtain a partial-area image which is good enough.

Further, in the system of the present embodiment, the picking of the cell in the incubation container is explained, but, the system of the present embodiment is useful also when a predetermined medicine is dropped onto the cell.

Further, in the system of each of the above-described embodiments, the pump part of the syringe 22 is electrically operated, so that the computer 50 judges the presence/absence of the completion notification of the picking based on the operation contents of the manipulator controller 21, but, when the pump part of the syringe 22 is not electrically operated, the user has to voluntarily input the completion notification of the picking.

Note that the input of the completion notification of the picking is performed through the aforementioned keyboard 56 and mouse 57, or a separately prepared input device. Alternatively, the input is performed through a specific operation part provided to the manipulator controller 21.

Further, although the micro imaging optical system 18 of each of the aforementioned embodiments detects only one type of the micro fluorescence image, it may also be modified to simultaneously detect a plurality of types of micro fluorescence images with different wavelengths. In such a case, the computer 50 synthesizes the plurality of types of micro fluorescence images obtained by the micro imaging optical system 18, by using mutually different colors, to create a color micro fluorescence image, and after performing processing on the image as described above, the computer 50 displays the resultant on the display 58.

Further, in the aforementioned embodiments, the operation of system when performing the picking of the cell is explained, but, the system can also be applied to manipulations other than the picking (injection, patch clamp and the like).

Further, in the system of each of the aforementioned embodiments, at least a part of the operation of the CPU 51 may also be executed by the controlling circuit 52. Further, in the system of each of the aforementioned embodiments, at least a part of the operation of the controlling circuit 52 may also be executed by the CPU 51.

Further, the inverted microscope 10, the manipulator 20, and the reserve stage 60 of the system of each of the aforementioned embodiments may also be disposed within an incubation apparatus. Note that the incubation apparatus corresponds to an apparatus with which a peripheral environment (carbon dioxide concentration, temperature, humidity and the like) of the incubation container is maintained as previously set.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be restored to, falling within the scope thereof.

What is claimed is:

1. A cell observing apparatus, comprising:
   an observation stage to support an incubation container that houses cells;
   a micro imaging optical system having an objective lens and, when the incubation container is supported by the observation stage and is disposed at an observing position of the observation stage, to form, on an imaging device for micro imaging via the objective lens of the micro imaging optical system, an image of the cells in the incubation container;
   a macro imaging optical system having imaging lenses and, when the incubation container is supported by the observation stage and is disposed at the observing position of the observation stage, to form, on an imaging device for macro imaging via the imaging lenses of the macro imaging optical system, an image of an area wider than that captured by the micro imaging optical system in the incubation container; and
   a controlling unit to control an operation of a manipulation needle that manipulates the cells in the incubation container, wherein
      an optical axis of the objective lens of the micro imaging optical system and an optical axis of the imaging lenses of the macro imaging optical system coincide with each other, and
      the micro imaging optical system and the macro imaging optical system are disposed on opposite sides of the observation stage and facing each other.

2. The cell observing apparatus according to claim 1, wherein
   the controlling unit moves the manipulation needle to a position at which a picking of at least one of the cells in the incubation container can be performed based on a wide image obtained by the imaging device for macro imaging and a partial image obtained by the imaging device for micro imaging.

3. The cell observing apparatus according to claim 1, wherein
   the controlling unit decides a focused cell being a cell to be focused among the cells in the incubation container based on an image analysis of a wide image obtained by the imaging device for macro imaging, calculates position coordinates of the focused cell, and then controls the manipulation needle based on the wide image obtained by the imaging device for macro imaging and a partial image obtained by the imaging device for micro imaging.

4. The cell observing apparatus according to claim 3, wherein
   the controlling unit moves the manipulation needle to the position coordinates of the focused cell being a manipulation target based on the wide image obtained by the imaging device for macro imaging, and makes the manipulation needle to be positioned at the position coordinates of the cell based on the partial image obtained by the imaging device for micro imaging when controlling the manipulation needle.

5. The cell observing apparatus according to claim 1, wherein
   when the incubation container is supported by the observation stage, the micro imaging optical system is disposed on a side of a bottom portion of the incubation container.

6. The cell observing apparatus according to claim 2, wherein
   the controlling unit controls the manipulation needle to perform a picking of a target cell from the incubation container based on the partial image obtained by the imaging device for micro imaging, and seeds the target cell obtained through the picking in another incubation container.

7. A cell incubation method being a cell incubation method of incubating cells using the cell observing apparatus according to claim 6, increasing a number of the target cell by repeatedly conducting:
   a step seeding the target cell obtained through the picking in the other incubation container, and then transferring the other incubation container to an incubator; and
   a step incubating the seeded target cell for a certain period of time in the incubator, and then returning the other incubation container to the cell observing apparatus.

8. The cell incubation method according to claim 7, wherein
   the target cell is an iPS cell.

9. A cell observing apparatus, comprising:
   an observation stage to support an incubation container that houses cells;
   a micro imaging optical system to, when the incubation container is supported by the observation stage and is disposed at an observing position of the observation stage, form, on an imaging device for micro imaging, an image of the cells in the incubation container;
   a macro imaging optical system to, when the incubation container is supported by the observation stage and is disposed at the observing position of the observation stage, form, on an imaging device for macro imaging, an image of an area wider than that captured by the micro imaging optical system in the incubation container;
   an oblique illuminating optical system to, when the incubation container is supported by the observation stage and is disposed at the observing position, illuminate the incubation container with an illumination luminous flux which is not parallel to optical axes of the macro imaging optical system and the micro imaging optical system and which thereby illuminates the incubation container so that the image formed by the macro imaging optical system and the image formed by the micro imaging optical system are formed simultaneously; and
   a controlling unit to control an operation of a manipulation needle that manipulates the cells in the incubation container.

10. The cell observing apparatus according to claim 9, wherein
the controlling unit displays, in real time, both of a wide dark-field image obtained by the imaging device for macro imaging during a period of time in which the oblique illuminating optical system illuminates the incubation container, and a partial dark-field image obtained by the imaging device for micro imaging during the period of time.

11. The cell observing apparatus according to claim 10, further comprising:
an excitation light illuminating optical system to irradiate excitation light to the cells in the incubation container; and
a storing unit to obtain, through the imaging device for micro imaging, partial fluorescence images from respective parts of the incubation container to which the excitation light is irradiated, and previously storing histories of the respective parts, wherein
the controlling unit reads the history of the part, in the incubation container, positioned on an optical axis of the micro imaging optical system, from the storing unit, and displays the history together with the partial dark-field image which is being displayed in real time.

12. The cell observing apparatus according to claim 11, wherein
the controlling unit displays the history as a movie image.

13. The cell observing apparatus according to claim 11, wherein
the controlling unit reads latest partial fluorescence images of the respective parts of the incubation container from the storing unit, and superimpose displays a guiding image in which the partial fluorescence images are connected, on the wide dark-field image which is being displayed in real time.

14. The cell observing apparatus according to claim 13, wherein
the controlling unit automatically adjusts the observation stage to make a manipulation target candidate position on the optical axis of the micro imaging optical system when the manipulation target candidate in the incubation container is designated on the guiding image.

15. The cell observing apparatus according to claim 13, wherein
the controlling unit highlights a manipulation target candidate on the guiding image when the manipulation target candidate in the incubation container is designated on the guiding image and a completion notification of manipulation with respect to the manipulation target candidate is input.

16. The cell observing apparatus according to claim 12, wherein
the controlling unit simultaneously displays the wide dark-field image obtained by the imaging device for macro imaging, the partial dark-field image obtained by the imaging device for micro imaging, and the movie image.

17. The cell observing apparatus according to claim 16, wherein
when an arbitrary cell is designated from the wide image, the controlling unit displays the movie image of the designated cell.

18. A cell incubation method of incubating cells, comprising:
micro imaging that performs a micro observation of a cell which is being incubated in a first incubation container, to obtain a partial image;
macro imaging that performs a macro observation of an area wider than that in said micro imaging in the first incubation container, to obtain a wide image;
judging that judges whether a state of the cell is good, based on the partial image;
picking that, when said judging judges that the state of the cell is good, controls, based on the wide image and the partial image, a manipulation needle to perform a picking up of the cell from the first incubation container;
seeding the cell picked up by the manipulation needle, in a second incubation container, and then transferring the second incubation container to an incubator;
incubating that incubates the seeded cell in the incubator for a certain period of time; and
for each of a plurality of respective cells being incubated in the first incubation container, repeating said micro imaging, said macro imaging, said judging, said picking, said seeding and said incubating, to thereby increase a number of cells judged to be good being incubated in the incubator.

19. The cell incubation method according to claim 18, wherein
in the picking, an XY coordinate position of the manipulation needle is made to coincide with an XY coordinate position of the cell based on the wide image obtained in the macro imaging, the manipulation needle is driven toward an XYZ coordinate position of the cell based on the partial image obtained in the micro imaging, and the cell is picked up by the manipulation needle.

20. The cell incubation method according to claim 18, wherein the cell is an iPS cell.

21. The cell observing apparatus according to claim 1, further comprising:
an oblique illuminating optical system to, when the incubation container is supported by the observation stage and is disposed at the observing position, illuminate the incubation container with an illumination luminous flux which is not parallel to the optical axis of the objective lens of the micro imaging optical system and is not parallel to the optical axis of the imaging lenses of the macro imaging optical system and which thereby illuminates the incubation container so that the image formed by the macro imaging optical system and the image formed by the micro imaging optical system are formed simultaneously.

* * * * *